(12) United States Patent
Choi et al.

(10) Patent No.: US 12,727,848 B2
(45) Date of Patent: Sep. 8, 2026

(54) ULTRASONIC DIAGNOSTIC APPARATUS, OPERATING METHOD THEREOF, AND RECORDING MEDIUM ON WHICH LEARNING ALGORITHM IS RECORDED

(71) Applicant: Samsung Medison Co., Ltd., Hongcheon-gun (KR)

(72) Inventors: Kwang Yeon Choi, Hongcheon-gun (KR); Jin Yong Lee, Hongcheon-gun (KR); Hye Sung Won, Seoul (KR); Mi Young Lee, Seoul (KR)

(73) Assignee: SAMSUNG MEDISON CO., LTD., Hongcheon-Gun (KR)

( * ) Notice: Subject to any disclaimer, the term of this patent is extended or adjusted under 35 U.S.C. 154(b) by 91 days.

(21) Appl. No.: 18/285,790

(22) PCT Filed: Sep. 2, 2021

(86) PCT No.: PCT/KR2021/011870
§ 371 (c)(1),
(2) Date: Oct. 5, 2023

(87) PCT Pub. No.: WO2022/215814
PCT Pub. Date: Oct. 13, 2022

(65) Prior Publication Data

US 2024/0180514 A1 Jun. 6, 2024

(30) Foreign Application Priority Data

Apr. 7, 2021 (KR) ........................ 10-2021-0045508

(51) Int. Cl.
*A61B 8/06* (2006.01)
*A61B 8/00* (2006.01)
*G01S 7/52* (2006.01)

(52) U.S. Cl.
CPC .............. *A61B 8/065* (2013.01); *A61B 8/463* (2013.01); *A61B 8/488* (2013.01); *A61B 8/54* (2013.01); *G01S 7/52057* (2013.01)

(58) Field of Classification Search
None
See application file for complete search history.

(56) References Cited

U.S. PATENT DOCUMENTS 6,450,959 B1 * 9/2002 Mo ..................... G01S 15/8979
600/455
8,303,507 B2 11/2012 Baba et al.
(Continued)

FOREIGN PATENT DOCUMENTS

JP 2006-102489 A 4/2006
JP 2010-200844 A 9/2010
(Continued)

OTHER PUBLICATIONS

International Search Report dated Jan. 3, 2022 issued in International Patent Application No. PCT/KR2021/011870 (with English translation).
(Continued)

*Primary Examiner* — Jonathan Cwern
(74) *Attorney, Agent, or Firm* — Morgan Lewis & Bockius LLP

(57) ABSTRACT

According to an embodiment, an ultrasonic diagnostic apparatus includes a control unit configured to analyze a shape of a Doppler waveform based on a Doppler signal, determine a type of the Doppler signal, determine at least one area of the Doppler waveform, calculate a similarity with respect to the at least one area, determine a measurement area based on the similarity, and calculate a measurement index based on
(Continued)

the measurement area, and a display unit displaying the Doppler waveform, the measurement area, and the measurement index.

20 Claims, 17 Drawing Sheets

(56) References Cited

U.S. PATENT DOCUMENTS

| | | | | |
|---|---|---|---|---|
| 10,631,828 | B1 | 4/2020 | Hare, II et al. | |
| 10,702,247 | B2 | 7/2020 | Hare, II et al. | |
| 2007/0055158 | A1* | 3/2007 | Jackson | A61B 8/08 600/443 |
| 2009/0149759 | A1* | 6/2009 | Baba | A61B 8/13 600/454 |
| 2009/0310837 | A1 | 12/2009 | Park et al. | |
| 2014/0046189 | A1* | 2/2014 | Jain | G16H 50/30 600/454 |
| 2014/0125691 | A1 | 5/2014 | Lysyansky | |
| 2017/0042513 | A1 | 2/2017 | Miyaji et al. | |
| 2019/0015077 | A1 | 1/2019 | Park et al. | |
| 2019/0209136 | A1 | 7/2019 | Lee et al. | |
| 2020/0060656 | A1 | 2/2020 | Chono | |
| 2022/0192627 | A1* | 6/2022 | Quattrone-Brown | A61B 8/14 |

FOREIGN PATENT DOCUMENTS

| | | | |
|---|---|---|---|
| JP | 5295684 | B2 | 9/2013 |
| JP | 5759591 | B1 | 6/2015 |
| JP | 6793077 | B2 | 12/2020 |
| KR | 10-2018-0031558 | A | 3/2018 |
| KR | 10-2019-0008055 | A | 1/2019 |

OTHER PUBLICATIONS

C. Ginghina, et al. "Doppler flow patterns in the evaluation of pulmonary hypertension," ResearchGate, Jan. 2009.

The Extended European Search Report dated Feb. 17, 2025 issued in European Patent Application No. 21936152.4.

R. Suresh, et al., "Automated Measurement of Fetal Right-Myocardial Performance Index from Pulsed Wave Doppler Spectrum," Samsung R&D Institute, Department of Obstetrics and Gynecology, Univ. of Ulsan College of Medicine, Proc. of SPIE, vol. 10950, 2019.

Office Action dated Oct. 29, 2025 issued in the corresponding Korean Patent Application No. 10-2021-0045508 with the English translation. (Note: JP 2006-102489 A, and US 2020-0060656 A1 already submitted.)

European Office Action dated Apr. 28, 2026 issued in European Patent Application No. 21936152.4.

* cited by examiner 100a
121
122
123
(a)
100b
121
122
165
124
172
171
(b)
100c
145
40
20
(c)

(a)

(b)

(a)

(b)

(a)

(b)

140
SS
MA1
MA2
141a
141b
143
TST 259.52
ET 178.57
ICT 35.71
IRT 45.24
MPI 0.45

ULTRASONIC DIAGNOSTIC APPARATUS, OPERATING METHOD THEREOF, AND RECORDING MEDIUM ON WHICH LEARNING ALGORITHM IS RECORDED

CROSS-REFERENCE OF RELATED APPLICATIONS

This application is the U.S. National Phase under 35 U.S.C. § 371 of International Patent Application No. PCT/KR2021/011870, filed on Sep. 2 2021, which in turn claims the benefit of Korean Application No. 10-2021-0045508, filed on Apr. 7, 2021, the disclosures of which applications are incorporated by reference herein.

TECHNICAL FIELD

The present disclosure relates to an ultrasonic diagnostic apparatus, an operating method thereof, and a recording medium on which a learning algorithm is recorded.

BACKGROUND ART

An ultrasonic diagnostic apparatus may provide at least one ultrasonic image of a part inside an object by irradiating an ultrasonic signal generated from a transducer of a probe onto the object, receiving a signal reflected from the object, and performing image processing on the signal.

Also, the ultrasonic diagnostic apparatus may measure the speed, direction, and the like of a moving object by using a Doppler effect and output a measurement index related to the measured speed, direction, and the like of the object.

When a measurement index of the object is output by receiving an input of a user, the measurement index may not be correct when the input of the user is wrong.

DISCLOSURE

Technical Problem

Provided are an ultrasonic diagnostic apparatus with improved accuracy of a measurement index calculated from a Doppler ultrasonic image and increased user convenience, an operating method thereof, and a recording medium on which a learning algorithm is recorded.

Advantageous Effects

In an ultrasonic diagnostic apparatus, an operating method thereof, and a recording medium on which a learning algorithm is recorded, according to the present disclosure, an inflow Doppler signal and an outflow Doppler signal may be automatically determined, and a measurement area and a measurement index may be automatically calculated based on an optimum inflow Doppler signal and an optimum outflow Doppler signal.

Accordingly, the accuracy of the measurement index calculated from a Doppler ultrasonic image may be improved and user convenience may be increased.

Figure 2:
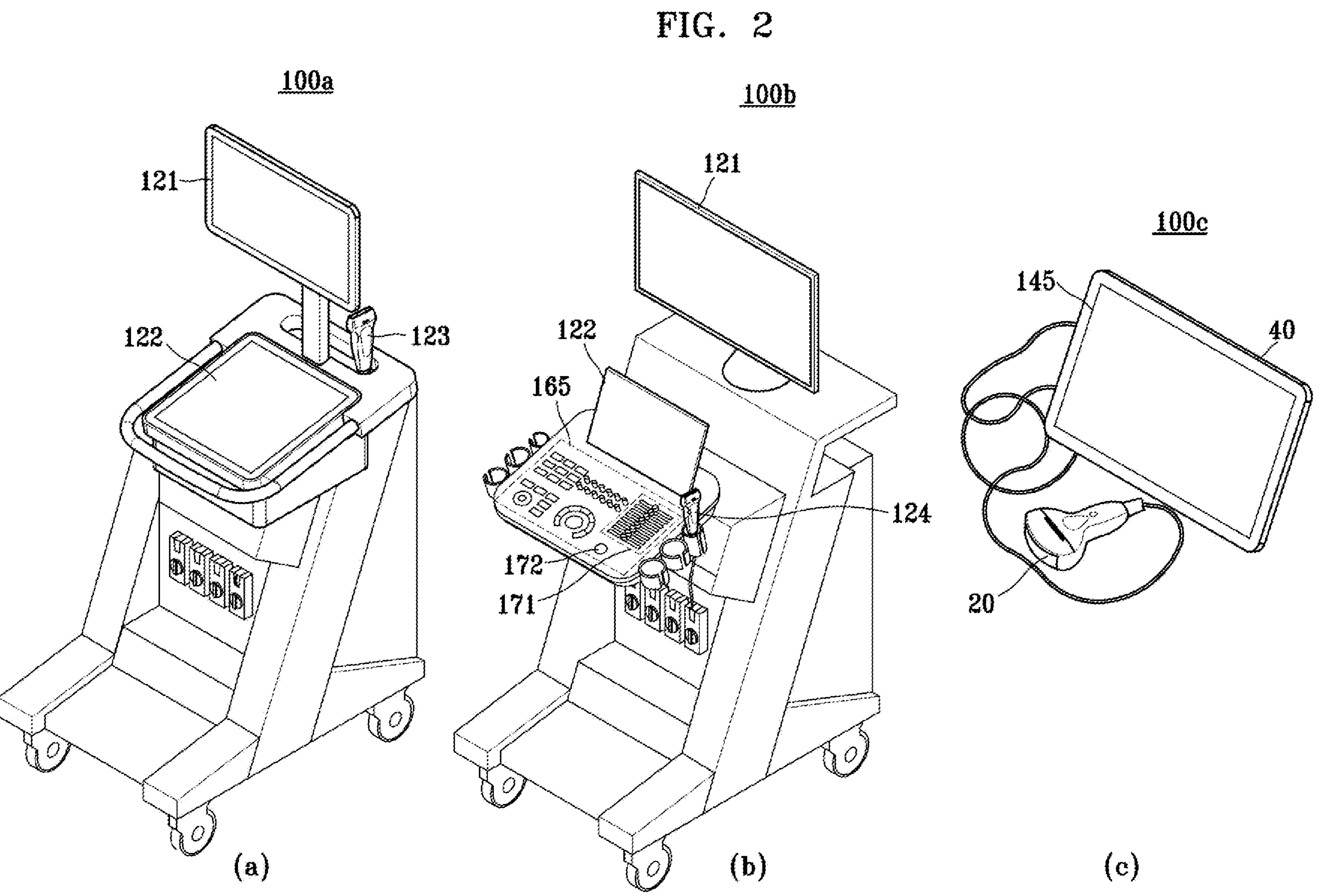

(a) to (c) of FIG. 2 are diagrams showing an ultrasonic diagnostic apparatus according to an embodiment.

Figure 3:
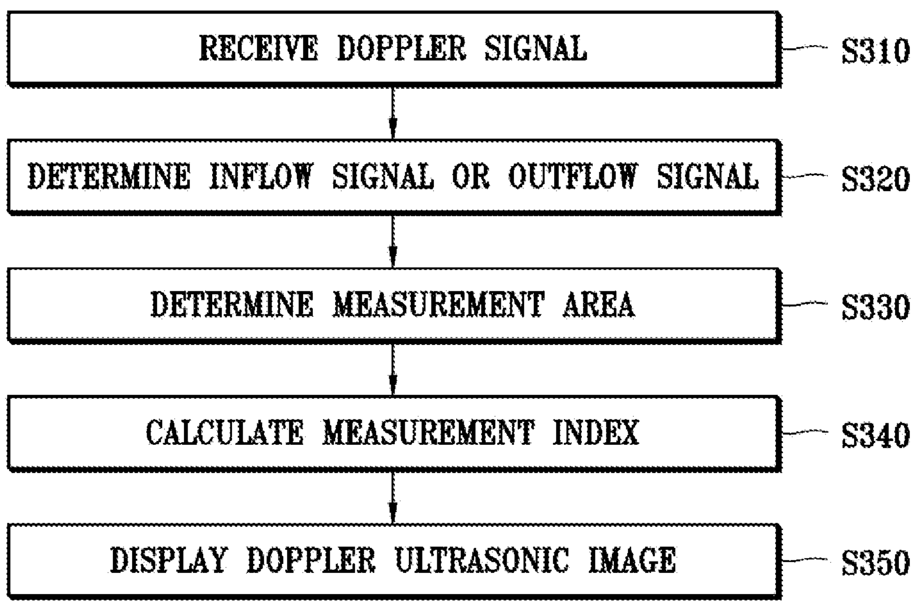

FIG. 3 is a flowchart of an operating method of an ultrasonic diagnostic apparatus, according to an embodiment.

Figure 4:
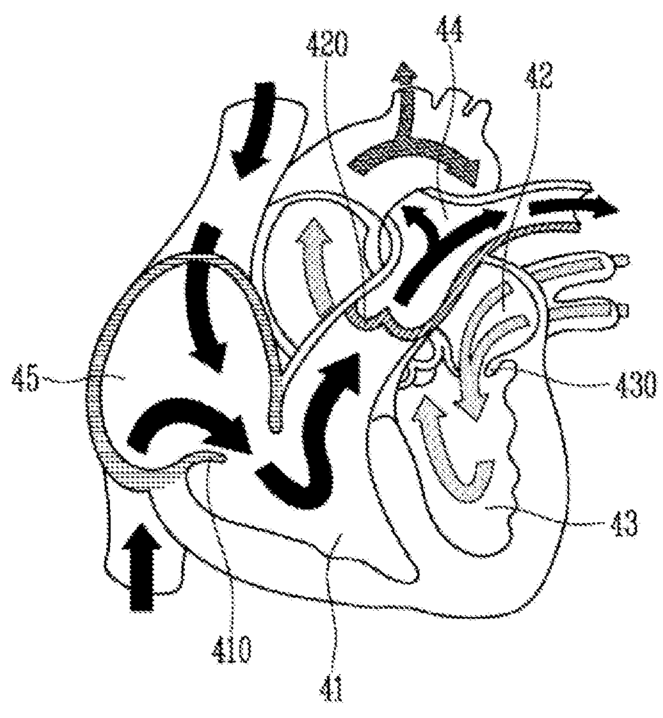

FIG. 4 is a diagram for describing a heart structure of a person among objects to which an ultrasonic diagnostic apparatus according to an embodiment is applied.

FIGS. 5, 6, 7, and 8 are diagrams for describing a method by which an ultrasonic diagnostic apparatus according to an embodiment analyzes a shape of a Doppler waveform.

FIGS. 9, 10, 11, and 12 are diagrams for describing a method by which an ultrasonic diagnostic apparatus according to an embodiment determines a Doppler signal suitable for measurement.

Figure 13:
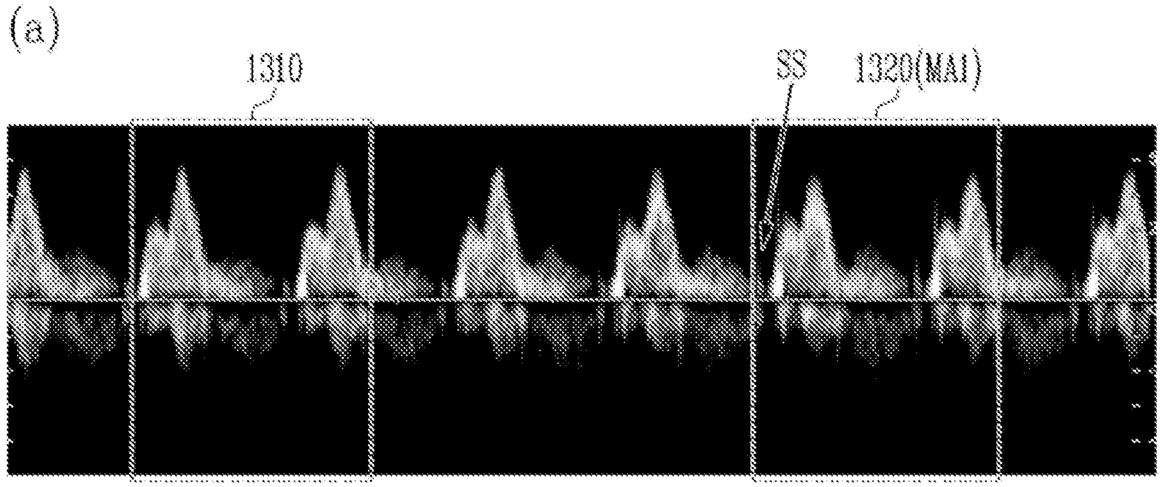
Figure 13:
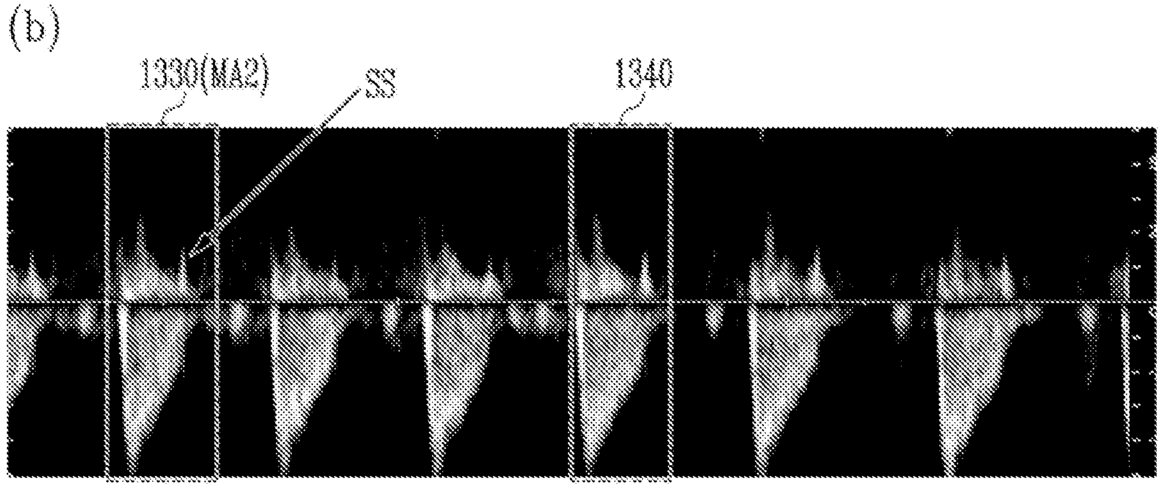

FIG. 13 is a diagram illustrating a first measurement area and a second measurement area being determined by an ultrasonic diagnostic apparatus according to an embodiment.

Figure 14:
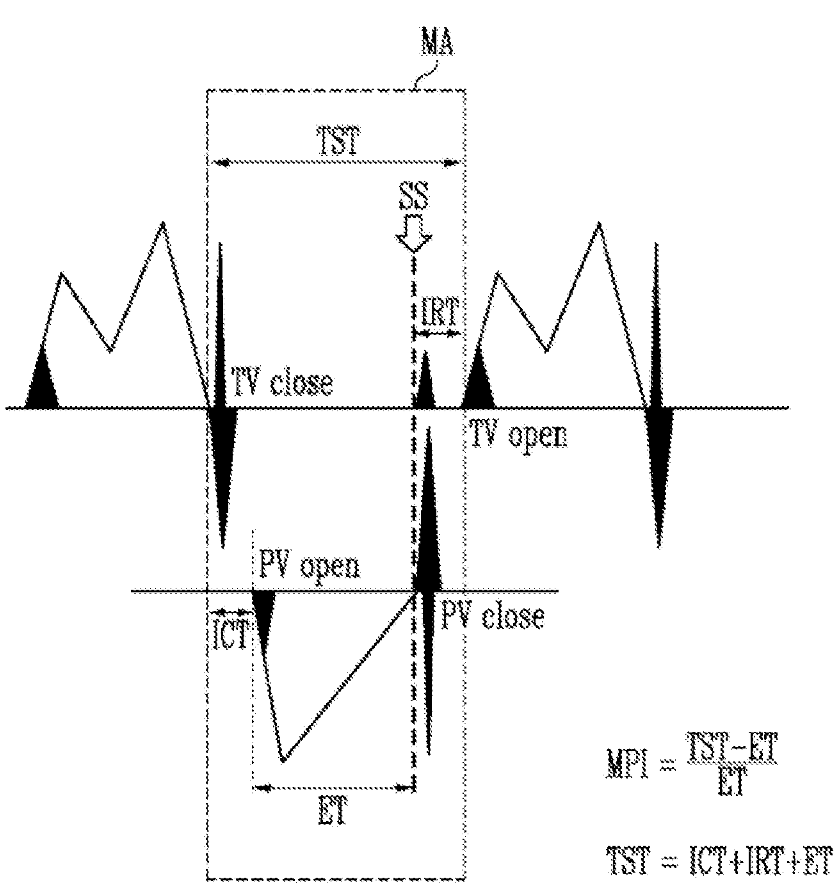

FIG. 14 is a diagram for describing a method by which an ultrasonic diagnostic apparatus according to an embodiment calculates a measurement index.

Figure 15:
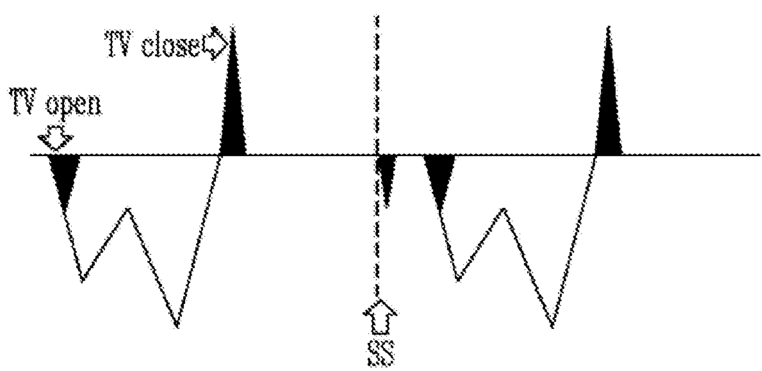

FIG. 15 is a diagram for describing a method by which an ultrasonic diagnostic apparatus according to an embodiment analyzes a shape of a Doppler waveform.

Figure 16:
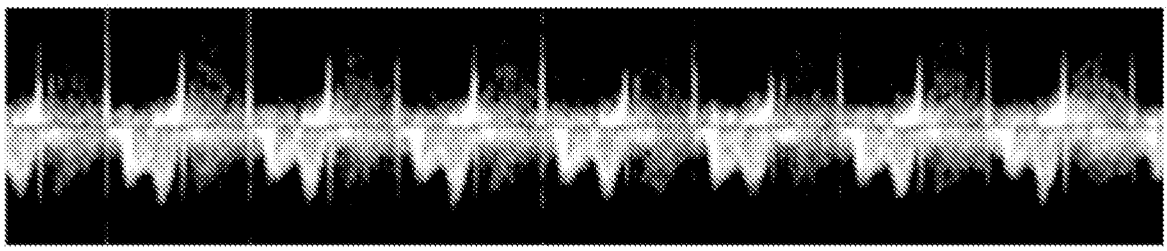
Figure 16:

FIG. 16 is a diagram for describing a method by which an ultrasonic diagnostic apparatus according to an embodiment determines a Doppler signal suitable for measurement.

Figure 17:
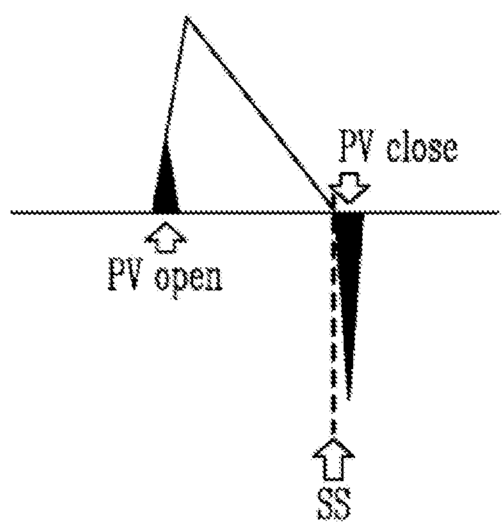

FIG. 17 is a diagram for describing a method by which an ultrasonic diagnostic apparatus according to an embodiment analyzes a shape of a Doppler waveform.

Figure 18:
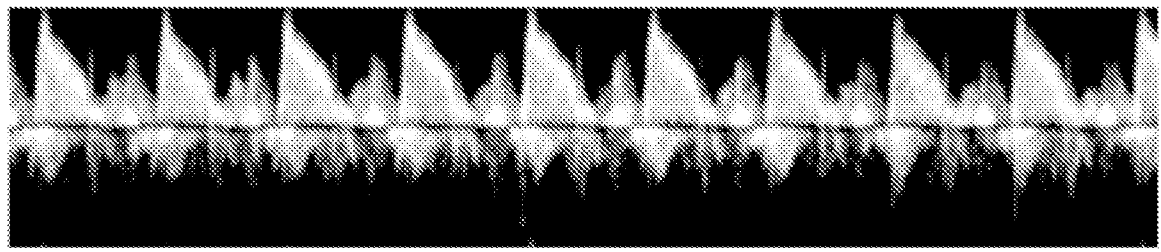
Figure 18:

FIG. 18 is a diagram for describing a method by which an ultrasonic diagnostic apparatus according to an embodiment determines a Doppler signal suitable for measurement.

Figure 19:
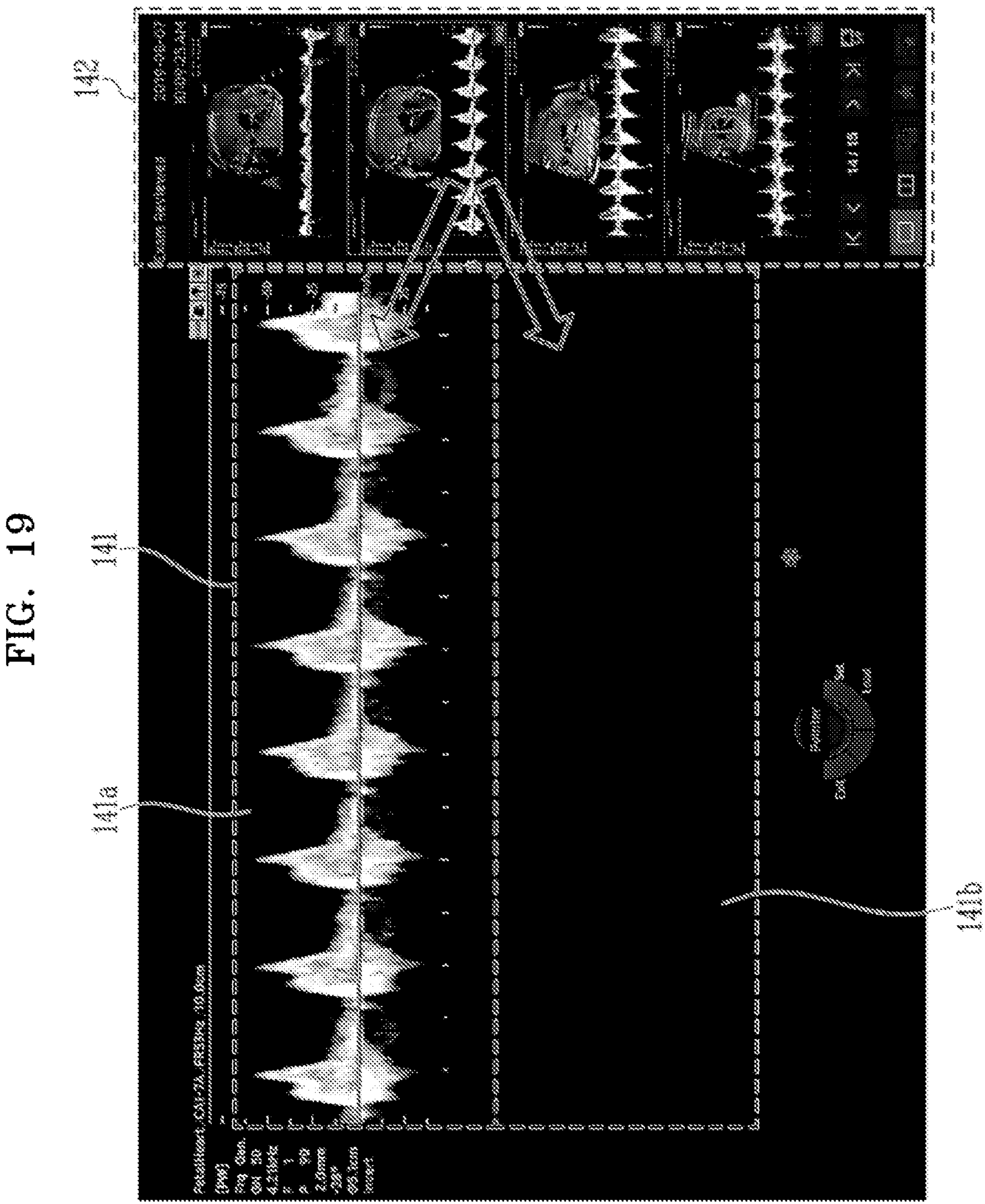

FIG. 19 is a diagram showing a Doppler ultrasonic image displayed on an ultrasonic diagnostic apparatus according to an embodiment.

Figure 20:
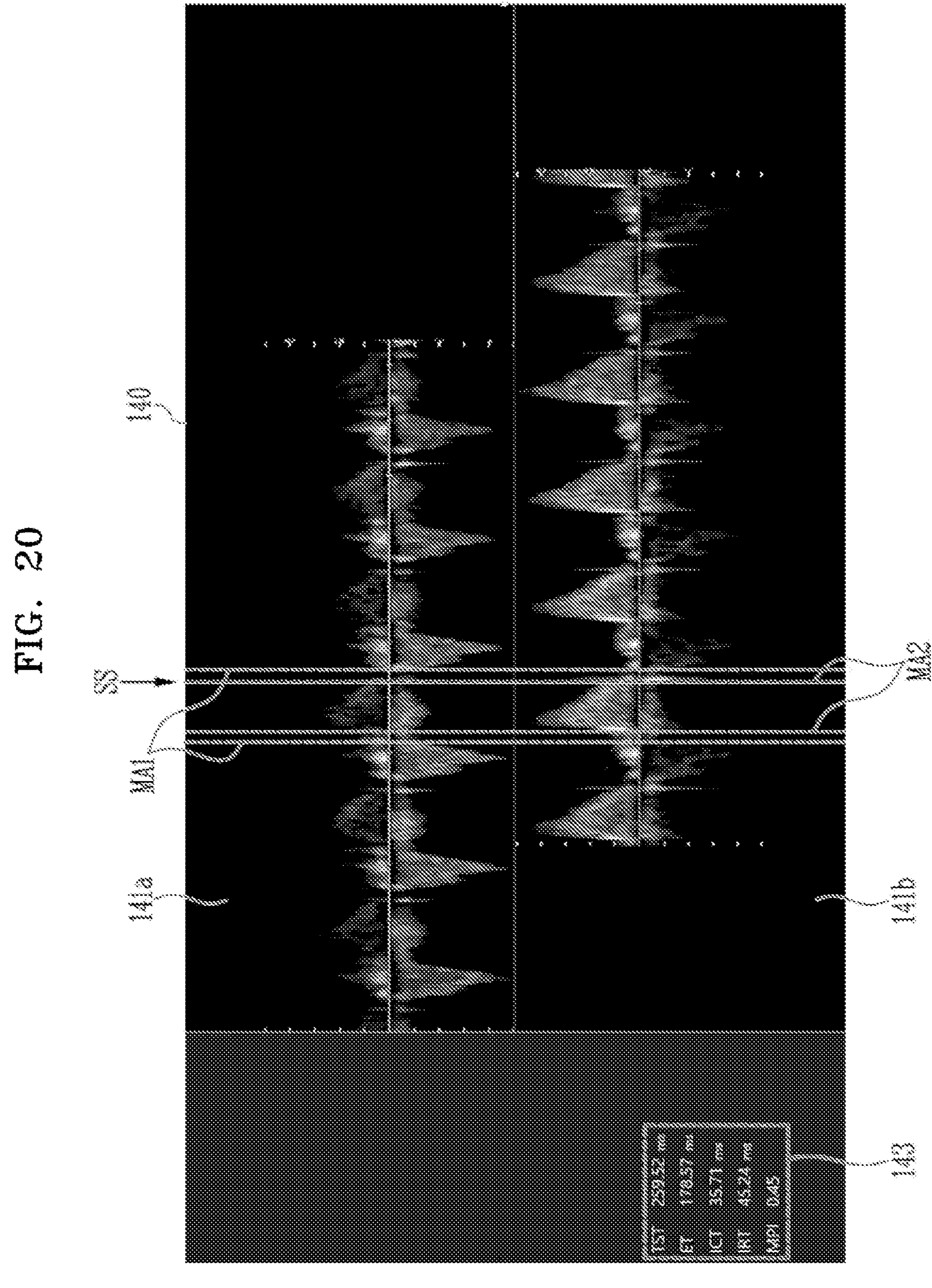

FIG. 20 is a diagram showing a Doppler ultrasonic image, a measurement area, and a measurement index displayed on an ultrasonic diagnostic apparatus according to an embodiment.

Figure 21:
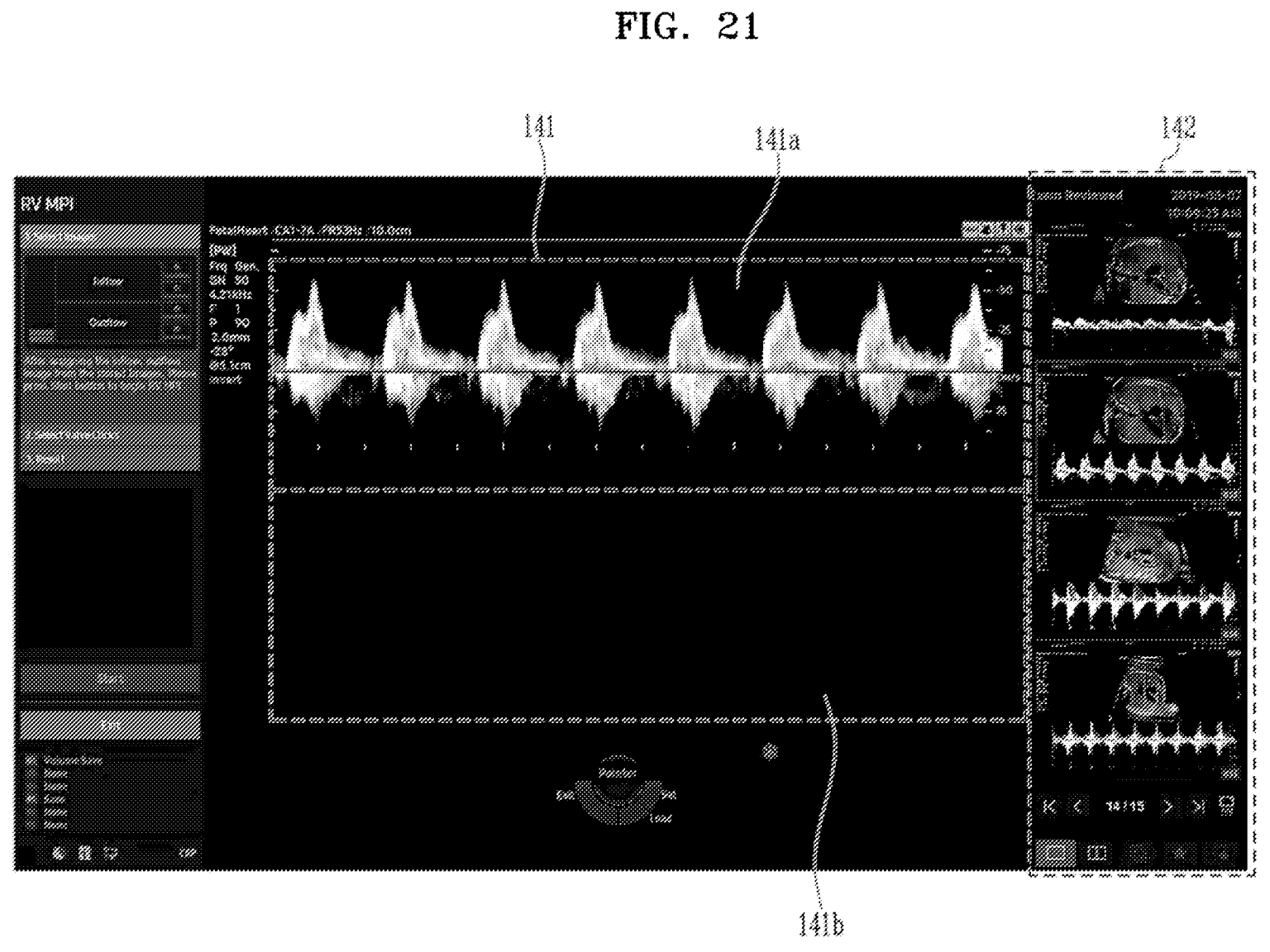

FIG. 21 is a diagram showing a Doppler ultrasonic image displayed on an ultrasonic diagnostic apparatus according to an embodiment.

Figure 22:
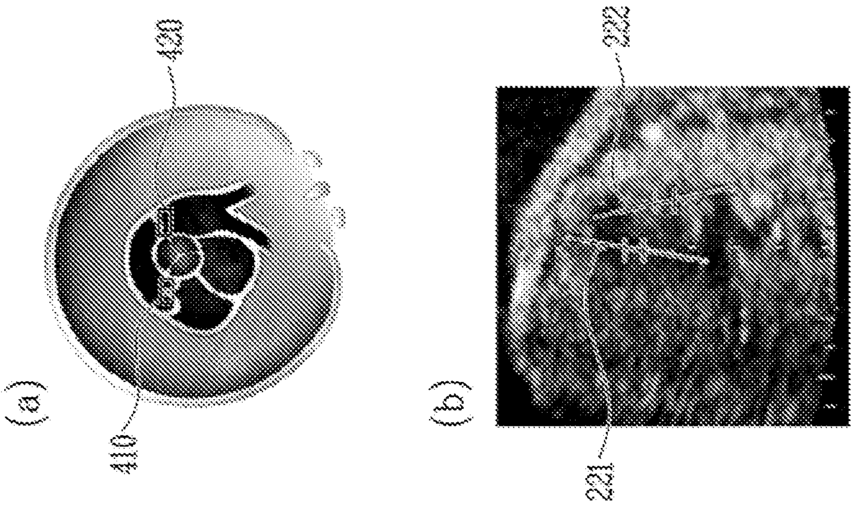

FIG. 22 is a diagram for describing a Doppler ultrasonic image displayed on an ultrasonic diagnostic apparatus according to an embodiment.

Figure 23:
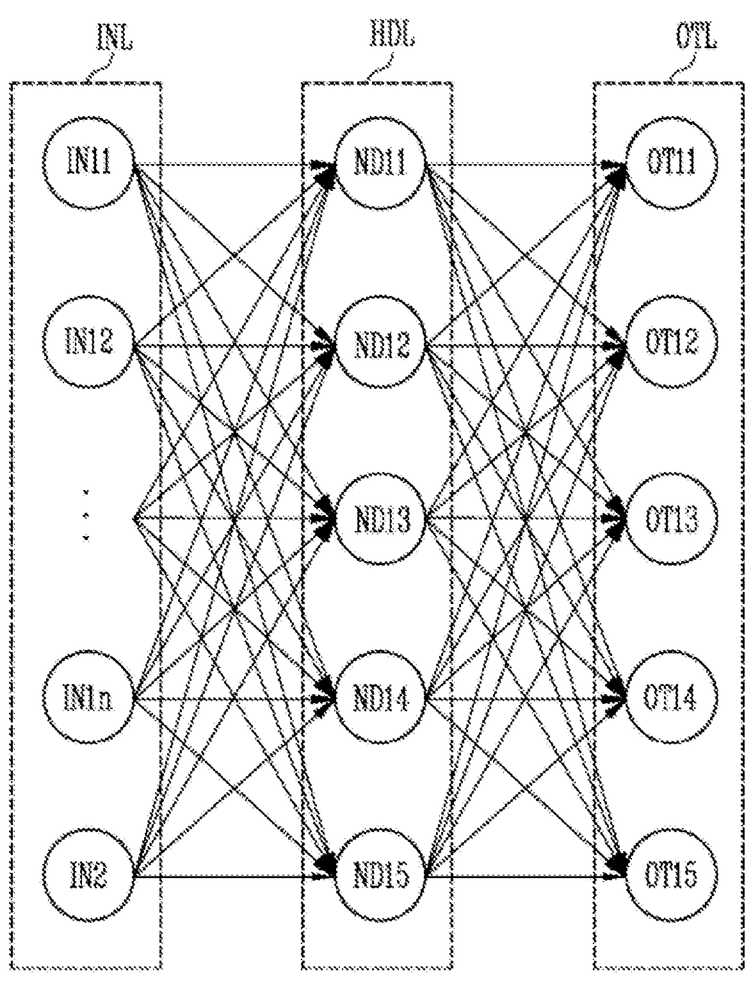

FIG. 23 is a diagram for describing a learning algorithm according to an embodiment.

BEST MODE

An ultrasonic diagnostic apparatus according to an embodiment includes a control unit configured to analyze a shape of a Doppler waveform based on a Doppler signal, determine a type of the Doppler signal, determine at least one area of the Doppler waveform, calculate a similarity with respect to the at least one area, determine a measurement area based on the similarity, and calculate a measurement index based on the measurement area, and a display unit configured to display the Doppler waveform, the measurement area, and the measurement index.

The control unit may be further configured to determine Doppler signal information with respect to the determined Doppler signal, and determine the at least one area of the Doppler waveform, based on the determined Doppler signal information.

The control unit may be further configured to determine a first Doppler signal when the shape of the Doppler waveform is "M" or "reversed M", and determine a second Doppler signal when the shape of the Doppler waveform is "V" or "reversed V".

The first Doppler signal may be a Doppler signal of blood flowing into the heart of an object, and the second Doppler signal may be Doppler signal of blood flowing out of the heart of the object.

The Doppler signal information may include first Doppler signal information about the first Doppler signal and second Doppler signal information about the second Doppler signal.

The first Doppler signal information may include an opening time of a tricuspid valve, a closing time of the tricuspid valve, and a location of a synchronization signal, and the second Doppler signal information may include an opening time of a pulmonary valve, a closing time of the pulmonary valve, and the location of the synchronization signal.

The control unit may be further configured to calculate the similarity by comparing the Doppler signal with a pre-learned Doppler signal for the at least one area.

The control unit may be further configured to calculate the similarity for the at least one area, based on a period of the Doppler waveform generated based on the Doppler signal, a cardiac cycle of an object, and a strength of the Doppler signal.

The measurement area may include a first measurement area and a second measurement area, the first measurement area may be an area based on the first Doppler signal, and the second measurement area may be an area based on the second Doppler signal.

The control unit may be further configured to determine one measurement area by matching a synchronization signal of the first measurement area to a synchronization signal of the second measurement area, and calculate the measurement index based on the one measurement area.

The measurement index may include at least one parameter related to a function of the heart.

The at least one parameter may include a tricuspid valve closing time (TST), a pulmonary valve opening time (ET), a cardiac systolic time (ICT), a cardiac diastolic time (IRT), and a myocardial performance index (MPI).

The display unit may further display the at least one parameter.

The display unit may include a first main display area, a second main display area, and a sub display area, the first main display area may display a first Doppler ultrasonic image based on the first Doppler signal, and the second main display area may display a second Doppler ultrasonic image based on the second Doppler signal.

The sub display area may display at least one first Doppler ultrasonic image or at least one second Doppler ultrasonic image.

When the first main display area displays the first Doppler ultrasonic image, the sub display area may display the at least one second Doppler ultrasonic image.

When the second main display area displays the second Doppler ultrasonic image, the sub display area may display the at least one first Doppler ultrasonic image.

Images displayed in the first main display area and the second main display area may be replaced by an image displayed in the sub display area.

The display unit may display a first sample volume gate and a second sample volume gate, and according to a location of the first sample volume gate or the second sample volume gate, the first main display area may display the first Doppler ultrasonic image and the second main display area may display the second Doppler ultrasonic image.

When one of the first sample volume gate and the second sample volume gate is located in correspondence to a tricuspid valve, the first main display area may display the first Doppler ultrasonic image, and when one of the first sample volume gate and the second sample volume gate is located in correspondence to a pulmonary valve, the second main display area may display the second Doppler ultrasonic image.

The at least one area may include a period of the Doppler waveform generated based on the Doppler signal.

An operating method of an ultrasonic diagnostic apparatus, according to an embodiment, includes receiving a Doppler signal, analyzing a shape of a Doppler waveform based on the Doppler signal and determining a type of the Doppler signal, determining at least one area of the Doppler waveform and calculating a similarity with respect to the at least one area, determining a measurement area based on the similarity, and calculating a measurement index based on the measurement area.

The operating method may further include displaying the Doppler waveform, the measurement area, and the measurement index.

The operating method may further include determining the type of the Doppler signal and determining Doppler signal information for the determined Doppler signal.

The operating method may further include determining the at least one area of the Doppler waveform, based on the determined Doppler signal information.

The similarity may be calculated by comparing the Doppler signal with a pre-learned Doppler signal for the at least one area.

One measurement area may be determined by matching synchronization signals of areas where the similarity is high, and the measurement index may be calculated based on the one measurement area.

A computer-readable recording medium may have recorded thereon a program for executing an operating method of an ultrasonic diagnostic apparatus according to an embodiment.

An operating method of an ultrasonic diagnostic apparatus, according to an embodiment, includes receiving a Doppler signal, analyzing a shape of a Doppler waveform based on the Doppler signal and determining a type of the Doppler signal, displaying a first Doppler ultrasonic image and/or a second Doppler ultrasonic image, according to the type of the Doppler signal, receiving identification on whether the first Doppler ultrasonic image corresponds to an image related to inflow bloodstream and the second Doppler ultrasonic image corresponds to an image related to outflow bloodstream, determining a first Doppler signal and a second Doppler signal, which have a high similarity with a pre-learned Doppler signal, displaying an inflow Doppler ultrasonic image and/or an outflow Doppler ultrasonic image based on the first Doppler signal and the second Doppler signal having the high similarity, receiving identification on whether the inflow Doppler ultrasonic image and/or the outflow Doppler ultrasonic image are appropriate, displaying a measurement area in the inflow Doppler ultrasonic image and/or the outflow Doppler ultrasonic image, receiving identification on whether the measurement area is appropriate, and displaying a measurement index calculated based on the measurement area.

The operating method may further include, when the first Doppler ultrasonic image does not correspond to the image related to the inflow bloodstream or the second Doppler ultrasonic image does not correspond to the image related to the outflow bloodstream, receiving a user input for replacing a Doppler ultrasonic image.

The operating method may further include, when the inflow Doppler ultrasonic image and/or the outflow Doppler ultrasonic image do not satisfy a pre-set standard, receiving a user input for replacing a Doppler ultrasonic image.

The operating method may further include, when the measurement area displayed in the inflow Doppler ultrasonic image and/or the outflow Doppler ultrasonic image is not appropriate, receiving a user input for replacing the measurement area.

An operating method of an ultrasonic diagnostic apparatus, according to an embodiment, includes receiving a Doppler signal, analyzing a shape of a Doppler waveform based on the Doppler signal and determining a type of the Doppler signal, displaying a first Doppler ultrasonic image and/or a second Doppler ultrasonic image, according to the type of the Doppler signal, determining a first Doppler signal and a second Doppler signal, which have a high similarity with a pre-learned Doppler signal, displaying a measurement area in the first Doppler ultrasonic image and/or the second Doppler ultrasonic image, and displaying a measurement index calculated based on the measurement area.

According to an embodiment, provided is a recording medium having recorded thereon a learning algorithm including at least one hidden layer between an input layer and an output layer, wherein the learning algorithm includes receiving a Doppler signal as first inputs of the input layer, and based on the first inputs, providing first outputs of the output layer so as to display a Doppler ultrasonic image and display a measurement area and a measurement index on the Doppler ultrasonic image.

MODE FOR INVENTION

Hereinafter, various embodiments of the present disclosure will be described in detail with reference to the accompanying drawings such that one of ordinary skill in the art may easily implement the present disclosure. The present disclosure may be implemented in various different forms and is not limited to embodiments described herein.

In order to clearly describe the present disclosure, parts that are not related to the description are omitted, and a same reference numeral or reference sign denote same or similar components throughout the specification. Accordingly, a reference numeral or reference sign mentioned previously may also be used for other drawings.

Also, because sizes and thicknesses of components in the drawings are arbitrarily illustrated for convenience of description, the present disclosure is not necessarily limited thereto. In the drawings, thicknesses may be exaggerated to clearly represent several layers and regions.

Also, in the description, "the same" may denote "substantially the same". In other words, the sameness would be to the extent that one of ordinary skill in the art can understand to be the same. Other expressions may also be expressions from which "substantially" is omitted.

The present specification describes the principles of the present disclosure and discloses embodiments such that the scope of right of the present disclosure is clarified and one of ordinary skill in the art may practice the present disclosure. The embodiments may be implemented in various forms.

Throughout the specification, when a part is "connected" to another part, the part may be connected to the other part directly or indirectly, and an indirect connection includes a connection through a wireless communication network.

Also, the terms used in the present specification are only used to describe embodiments, and are not intended to limit and/or restrict the present disclosure. An expression used in the singular encompasses the expression in the plural, unless it has a clearly different meaning in the context. In the present specification, the terms such as "including" or "having", etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Also, the terms including ordinal numbers, such as "first" and "second", used in the present specification may be used to describe various components, but the components are not limited by the terms and the terms are used only to distinguish one component from another component. For example, without departing from the scope of the rights described in the present disclosure, a first component may be referred to as a second component, and similarly, a second component may be referred to as a first component.

The terms such as "unit", "-er/or", block", "member", and "module" may denote a unit processing at least one function or operation. For example, the terms may denote at least one piece of hardware, such as a field-programmable gate array (FPGA)/an application specific integrated circuit (ASIC), at least one piece of software stored in a memory, or at least one process processed by a processor.

Reference signs or reference numerals attached to operations are used to identify the operations and do not describe the order of operations, and the operations may be executed in the order different from a stated order unless a specific order is explicitly stated in context.

In the present specification, an image may include a medical image obtained by a medical imaging device, such as a magnetic resonance imaging (MRI) device, a computed tomography (CT) device, an ultrasonographic imaging device, or an X-ray imaging device.

Also, in the present specification an "object" may be a target to be photographed and may include a person, an animal, or a part thereof. For example, the object may include a body part (an organ) or a phantom.

Throughout the specification, an "ultrasonic image" denotes an image of an object, which is processed based on an ultrasonic signal transmitted to the object and reflected from the object.

Also, throughout the specification, a "Doppler signal" may denote an ultrasonic signal, ultrasonic data, or Doppler data reflected from an object. A "Doppler waveform" may denote a shape of a Doppler signal. "Doppler signal information" may include a cardiac cycle of an object, a starting point (or a begin signal or a click signal) constituting the cardiac cycle of the object, and a peak point of a waveform according to a signal. Here, the "Doppler signal information" and the "Doppler waveform" are data related to the "Doppler signal" and may be concepts included in the "Doppler signal".

Hereinafter, embodiments of the present disclosure will be described with reference to accompanying drawings.

Figure 1:
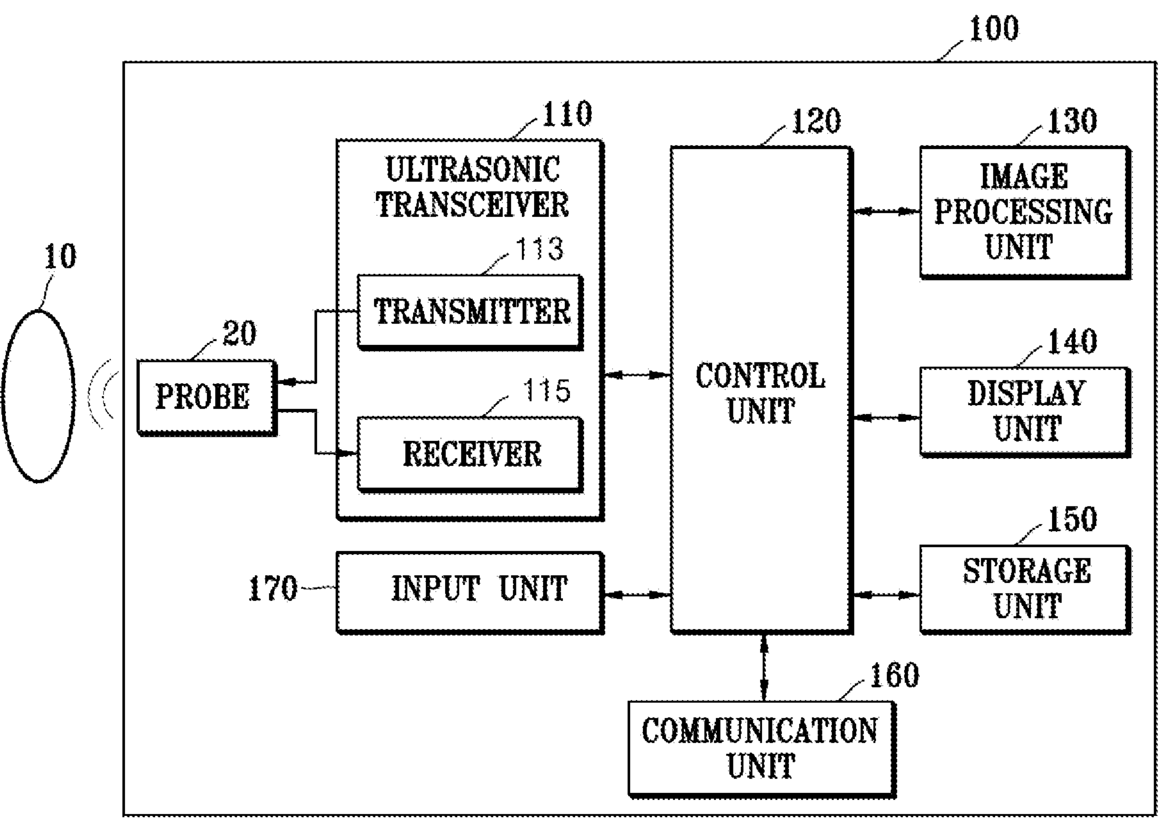
FIG. 1 is a block diagram of a configuration of an ultrasonic diagnostic apparatus, according to an embodiment.

FIG. 1 is a block diagram of a configuration of an ultrasonic diagnostic apparatus, according to an embodiment. An ultrasonic diagnostic apparatus 100 according to an embodiment may include a probe 20, an ultrasonic transceiver 110, a control unit 120, an image processing unit 130, a display unit 140, a storage unit 150, a communication unit 160, and an input unit 170.

The ultrasonic diagnostic apparatus 100 may be realized not only as a cart type but also as a portable type. Examples of a portable type ultrasonic diagnostic apparatus may include a smartphone, a laptop computer, a personal digital assistant (PDA), and a tablet personal computer (PC), which include a probe and an application, but are not limited thereto.

The probe 20 may include a plurality of transducers. The plurality of transducers may transmit an ultrasonic signal to an object 10 according to a transmission signal applied from a transmitter 113. The plurality of transducers may receive the ultrasonic signal reflected from the object 10 to form a reception signal. The probe 20 may be implemented as an integrated type with the ultrasonic diagnostic apparatus 100 or as a separated type connected to the ultrasonic diagnostic apparatus 100 wirelessly or via wires. Also, the ultrasonic diagnostic apparatus 100 may include one or a plurality of probes 20, according to an embodiment.

The control unit 120 controls the transmitter 113 to form the transmission signal to be applied to each of the plurality of transducers included in the probe 20, considering locations and focused points of the plurality of transducers.

The control unit 120 controls a receiver 115 to generate ultrasonic data by performing analog-digital conversion on the reception signals received from the probe 20 and adding the digital-converted reception signals, considering the locations and focused points of the plurality of transducers.

The image processing unit 130 generates an ultrasonic image by using the ultrasonic data generated by the receiver 115.

The display unit 140 may display the generated ultrasonic image and various types of information processed by the ultrasonic diagnostic apparatus 100. The ultrasonic diagnostic apparatus 100 may include one or a plurality of display units 140, according to an embodiment. Also, the display unit 140 may be realized as a touch screen by being combined with a touch panel.

The control unit 120 may control all operations of the ultrasonic diagnostic apparatus 100 and signal flow between internal components of the ultrasonic diagnostic apparatus 100. The control unit 120 may include a memory storing a program or data for performing functions of the ultrasonic diagnostic apparatus 100, and a processor processing the program or data. Also, the control unit 120 may receive a control signal from the input unit 170 or an external device and control operations of the ultrasonic diagnostic apparatus 100.

The ultrasonic diagnostic apparatus 100 includes the communication unit 160 and may be connected to the external device (e.g., a server, a medical device, a portable device (a smartphone, a tablet PC, or a wearable device)) through the communication unit 160.

The communication unit 160 may include one or more components enabling communication with the external device, and for example, may include at least one of a short-range communication module, a wired communication module, and a wireless communication module.

The communication unit 160 may receive a control signal and data from the external device and transmit the received control signal to the control unit 120 such that the control unit 120 controls the ultrasonic diagnostic apparatus 100 according to the received control signal.

Alternatively, the control unit 120 may transmit the control signal to the external device through the communication unit 160 to control the external device according to the control signal of the control unit 120.

For example, the external device may process data of the external device according to a control signal of a control unit of the external device, which is received through a communication unit of the external device.

A program (artificial intelligence or the like) for controlling the ultrasonic diagnostic apparatus 100 may be installed in the external device, and the program may include instructions performing some or all of operations of the control unit 120.

The program may be pre-installed in the external device or may be downloaded and installed by a user of the external device from a server providing an application. The server providing the application may include a recording medium storing the program.

Also, the program may include a storage medium of a server or a storage medium of a client device in a system including the server and the client device. Alternatively, when there is a third device (a smartphone, a tablet PC, or a wearable device) that communicates with the server or the client device, a program product may include a storage medium of the third device. Alternatively, the program may include a software program transmitted from the server to the client device or the third device, or transmitted from the third device to the client device.

In this case, one of the server, the client device, and the third device may perform a method according to embodiments by executing the program. Alternatively, two or more of the server, the client device, and the third device may execute the program to perform the method according to the embodiments in a distributed fashion.

For example, the server, for example, a cloud server or an artificial intelligence server, may execute the program stored in the server to control the client device communicatively connected to the server to perform the method according to the embodiments.

The storage unit 150 may store various types of data or programs for driving and controlling the ultrasonic diagnostic apparatus 100, the input/output ultrasonic data, and the obtained ultrasonic image.

The input unit 170 may receive a user input for controlling the ultrasonic diagnostic apparatus 100. For example, the user input may include an input of manipulating a button, a keypad, a mouse, a track ball, a jog switch, or a knop, an input of touching a touchpad or a touch screen, a speech input, a motion input, or a biometric information input (e.g., iris recognition or fingerprint recognition).

Examples of the ultrasonic diagnostic apparatus 100 according to an embodiment will be described below through (a) to (c) of FIG. 2.

(a) to (c) of FIG. 2 are diagrams showing an ultrasonic diagnostic apparatus according to an embodiment.

Referring to (a) of FIG. 2 and (b) of FIG. 2, ultrasonic diagnostic apparatuses 100*a* and 100*b* may include a main display unit 121 and a sub display unit 122. One of the main display unit 121 and the sub display unit 122 may be realized as a touch screen. The main display unit 121 and the sub display unit 122 may display an ultrasonic image or various types of information processed by the ultrasonic diagnostic apparatuses 100*a* and 100*b*. Also, the main display unit 121 and the sub display unit 122 may be realized as a touch screen and provide a graphical user interface (GUI) to receive, from a user, data for controlling the ultrasonic diagnostic apparatuses 100*a* and 100*b*. For example, the main display unit 121 may display the ultrasonic image and the sub display unit 122 may display, in the form of GUI, a control panel for controlling the displaying of the ultrasonic image. The sub display unit 122 may receive data for controlling display of an image, through the control panel displayed as a GUI. The ultrasonic diagnostic apparatuses 100*a* and 100*b* may control display of the ultrasonic image displayed on the main display unit 121, by using input control data.

Referring to (b) of FIG. 2, the ultrasonic diagnostic apparatus 100*b* may further include a control panel 165 in addition to the main display unit 121 and the sub display unit 122. The control panel 165 may include a button, a track ball, a jog switch, and a knop, and receive data for controlling the ultrasonic diagnostic apparatus 100*b* from the user. For example, the control panel 165 may include a time gain compensation (TGC) button 171, a freeze button 172, and the like. The TGC button 171 is a button for setting a TGC value for each depth of the ultrasonic image. Also, when an input of the freeze button 172 is detected while scanning the ultrasonic image, the ultrasonic diagnostic apparatus 100*b* may maintain a state of a frame image being displayed at a corresponding time point.

Meanwhile, the button, the track ball, the jog switch, and the knop included in the control panel 165 may be provided to the main display unit 121 or the sub display unit 122 as a GUI.

Referring to (c) of FIG. 2, an ultrasonic diagnostic apparatus 100*c* may be realized as a portable type. Examples of the portable type ultrasonic diagnostic apparatus 100*c* may include a smartphone, a laptop computer, a PDA, and a tablet PC, which include a probe and an application, but are not limited thereto.

The ultrasonic diagnostic apparatus 100*c* includes the probe 20 and a main body 40, and the probe 20 may be connected to one side of the main body 40 via wires or wirelessly. The main body 40 may include a touch screen 145. The touch screen 145 may display an ultrasonic image, various types of information processed by the ultrasonic diagnostic apparatus, and a GUI.

Hereinafter, an operating method of an ultrasonic diagnostic apparatus, according to an embodiment, will be described with reference to FIG. 3.

FIG. 3 is a flowchart of the operating method of the ultrasonic diagnostic apparatus, according to an embodiment. Hereinafter, an embodiment is described with reference to the components and the reference numerals described with reference to FIGS. 1 and 2.

Referring to FIG. 3, in the ultrasonic diagnostic apparatus 100 according to an embodiment, the control unit 120 may receive, from the ultrasonic transceiver 110, a Doppler signal (or ultrasonic data or Doppler data) of an object (S310). Also, the control unit 120 may receive, from the image processing unit 130, an ultrasonic image (or a Doppler ultrasonic image).

The control unit 120 may analyze a shape of a Doppler waveform based on the Doppler signal to determine the Doppler signal as one of a first Doppler signal (or an inflow Doppler signal) and a second Doppler signal (or an outflow Doppler signal) (S320). Here, the first Doppler signal may be a Doppler signal of blood flowing into a heart of the object, and the second Doppler signal may be Doppler signal of blood flowing out of the heart of the object.

The control unit 120 may determine the first Doppler signal when the shape of the Doppler waveform has an "M" pattern or a "reversed M" pattern. The control unit 120 may determine the second Doppler signal when the shape of the Doppler waveform has a "V" pattern or a "reversed V" pattern.

The control unit 120 may determine Doppler signal information based on the Doppler signal. The Doppler signal information may include a cardiac cycle of the object, a starting point (or a begin signal or a click signal) constituting the cardiac cycle of the object, and a peak point of a waveform according to a signal.

In detail, the control unit 120 may determine first Doppler signal information (or inflow Doppler signal information) based on the first Doppler signal. For example, the first Doppler signal information may include an opening time of a tricuspid valve, a closing time of the tricuspid valve, and a location of a synchronization signal.

Also, the control unit 120 may determine second Doppler signal information (or an outflow Doppler signal information) based on the second Doppler signal. For example, the second Doppler signal information may include an opening time of a pulmonary valve, a closing time of the pulmonary valve, and the location of the synchronization signal.

The control unit 120 may determine at least one area of the Doppler waveform, based on the determined Doppler signal information. The display unit 140 may display the at least one area of the Doppler waveform. Here, the at least one area may be an area located between two straight lines.

In detail, the control unit 120 may determine a plurality of areas for a first Doppler waveform (or an inflow Doppler waveform), based on the determined first Doppler signal information. In other words, the plurality of areas may be determined according to the opening time of the tricuspid valve, the closing time of the tricuspid valve, and the location of the synchronization signal.

Also, the control unit 120 may determine a plurality of areas for a second Doppler waveform (or an outflow Doppler waveform), based on the determined second Doppler signal information. In other words, the plurality of areas may be determined according to the opening time of the pulmonary valve, the closing time of the pulmonary valve, and the location of the synchronization signal.

The control unit 120 may calculate a similarity by comparing the Doppler signal with a pre-learned Doppler signal for each of the plurality of areas. Also, the control unit 120 may calculate the similarity of each area, based on a period of the Doppler waveform generated based on the Doppler signal, a cardiac cycle, and a strength of the Doppler signal. The control unit 120 may determine that a Doppler signal of an area having a high calculated similarity corresponds to a Doppler signal suitable for measurement.

The control unit 120 may determine a measurement area in a Doppler ultrasonic image, based on the similarity (S330). The display unit 140 may display the determined measurement area in the Doppler ultrasonic image. The area between the two straight lines displayed in the Doppler ultrasonic image may be the determined measurement area.

In detail, the control unit 120 may determine a first measurement area in the inflow Doppler ultrasonic image, based on the similarity. Also, the control unit 120 may determine a second measurement area in the outflow Doppler ultrasonic image, based on the similarity.

The control unit 120 may determine one measurement area by matching the synchronization signal of the first measurement area to the synchronization signal of the second measurement area. In other words, the control unit 120 may calculate a measurement index based on one measurement area (S340).

The display unit 140 may receive, from the control unit 120, information about the first Doppler ultrasonic image, the second Doppler ultrasonic image, the measurement area, and the measurement index.

Accordingly, the display unit 140 may display the first Doppler ultrasonic image (or the first Doppler waveform), the second Doppler ultrasonic image (or the second Doppler waveform), the measurement area, and the measurement index (S350).

When the control unit 120 determines a type of the Doppler signal by analyzing the shape of the Doppler waveform, the display unit 140 may display the first Doppler ultrasonic image based on the first Doppler signal and/or the second Doppler ultrasonic image based on the second Doppler signal. Here, the user may identify whether the first Doppler ultrasonic image displayed on the display unit 140 corresponds to an image about inflow bloodstream and the second Doppler ultrasonic image corresponds to an image about an outflow bloodstream. When the first Doppler ultrasonic image displayed on the display unit 140 is not the inflow Doppler ultrasonic image and the second Doppler ultrasonic image is not the outflow Doppler ultrasonic image, the user may replace the Doppler ultrasonic image displayed on the display unit 140 through the input unit 170.

When the control unit 120 determines the first Doppler signal and the second Doppler signal, which have a high similarity with the pre-learned Doppler signal, the display unit 140 may display the first Doppler ultrasonic image and/or the second Doppler ultrasonic image, based on the first Doppler signal and the second Doppler signal having the high similarity. Here, the user may identify whether the first Doppler ultrasonic image and/or the second Doppler ultrasonic image, which have a high similarity, displayed on the display unit 140 are suitable (or match the user's standard or match a pre-set standard). For example, the user may identify whether the first Doppler ultrasonic image and/or the second Doppler ultrasonic image correspond to a clear image for calculating the measurement index. When the first and second Doppler ultrasonic images displayed on the display unit 140 are not suitable to the user's standard, the user may replace the Doppler ultrasonic image displayed on the display unit 140 through the input unit 170.

The display unit 140 may display the first Doppler ultrasonic image and/or the second Doppler ultrasonic image together in the measurement area. Here, the user may identify whether the measurement area displayed on the display unit 140 is suitable. When the measurement area displayed on the display unit 140 is not a suitable measurement area for calculating the measurement index, the user may replace the measurement area displayed on the display unit 140 through the input unit 170.

In other words, according to an embodiment, the ultrasonic diagnostic apparatus 100 may automatically determine the inflow Doppler signal and the outflow Doppler signal, and automatically calculate the measurement area and the measurement index, based on an optimum inflow Doppler signal and an optimum outflow Doppler signal. Accordingly, the accuracy of the measurement index calculated from the Doppler ultrasonic image may be improved and user convenience may be increased. Also, the user may identify the determined type of Doppler signal, the optimum Doppler ultrasonic image, and the measurement area, and replace the same.

Hereinafter, an object to which an ultrasonic diagnostic apparatus is applied will be described with reference to FIG. 4.

FIG. 4 is a diagram for describing a heart structure of a person among objects to which an ultrasonic diagnostic apparatus according to an embodiment is applied.

Referring to FIG. 4, the heart of the person is an organ that transfers blood all over the body. Blood vessels through which blood exits (or flows out) from the heart are called arteries, and blood vessels through which blood enters (or flows in) the heart are called veins. Blood circulates the body in the order of the right atrium, the right ventricle, the lungs, the left atrium, the left ventricle, the body, and the right atrium. The blood vessels flowing out from the heart are the pulmonary artery and the main artery. The blood vessels flowing into the heart are the superior vena cava, inferior vena cava, and the pulmonary vein.

The heart includes the right atrium 45, the right ventricle 41, the left atrium 42, the left ventricle 43, the tricuspid valve (TV) 410, the pulmonary valve (PV) 420, and the bicuspid valve 430.

The TV 410 is a valve located between the right atrium 45 and the right ventricle 41, and prevents blood from flowing backwards from the right ventricle 41 to the right atrium 45. Diseases associated with the TV 410 include TV stenosis, tricuspid insufficiency, Epstein's anomaly, and TV endocarditis.

The PV 420 is a valve located between the right ventricle 41 and the pulmonary artery 44, and prevents blood from flowing backwards from the pulmonary artery 44 to the right ventricle 41. Diseases associated with the PV 420 include PV stenosis, pulmonary insufficiency, aortic stenosis, and aortic insufficiency.

According to an embodiment, a shape of a Doppler waveform may be analyzed from a Doppler signal, and a closing time of the TV 410, an opening time of the TV 410, a closing time of the PV 420, an opening time of the PV 420, and the like may be determined to be used to calculate a TV closing time, a PV opening time, a cardiac systolic time, a cardiac diastolic time, and a myocardial performance index.

Hereinafter, a method of analyzing a shape of a Doppler waveform will be described with reference to FIGS. 5 to 7.

FIGS. 5, 6, 7, and 8 are diagrams for describing a method by which an ultrasonic diagnostic apparatus according to an embodiment analyzes a shape of a Doppler waveform. Hereinafter, an embodiment is described with reference to the components and the reference numerals described with reference to FIGS. 1 to 4.

Figure 5:
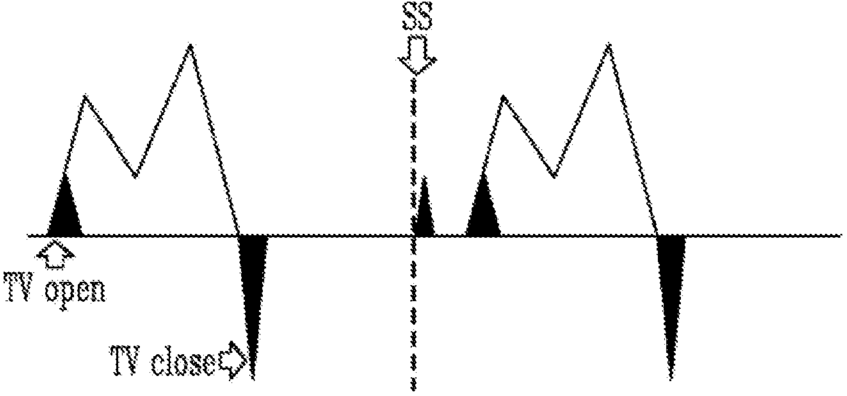
Figure 6:
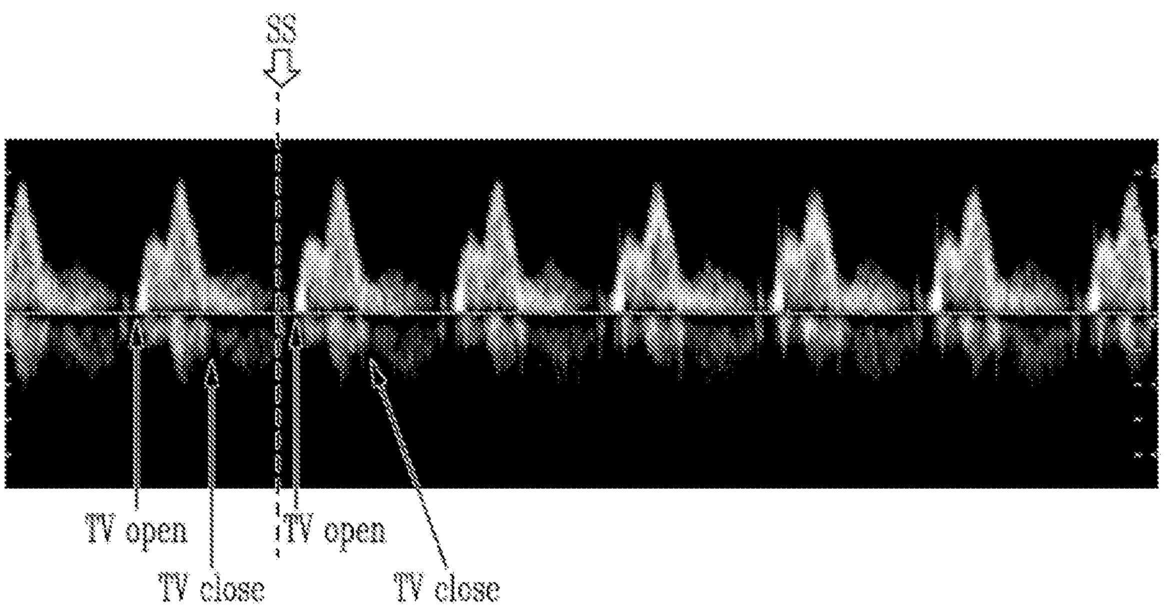

Referring to FIG. 5, a schematic diagram of the Doppler waveform is illustrated, and referring to FIG. 6, consecutive Doppler ultrasonic images (or Doppler waveforms) are illustrated. The Doppler ultrasonic image may be generated through the control unit 120 (see FIG. 1) and/or the image processing unit 130 (see FIG. 1) as the receiver 115 (see FIG. 1) receives the generated ultrasonic data (or the Doppler signal).

The Doppler waveform shown in FIGS. 5 and 6 may have an "M" pattern. The Doppler waveform having the "M" pattern may be generated based on blood flowing into the right ventricle 41 (see FIG. 4). In other words, the Doppler waveform having the "M" pattern may be generated based on the Doppler signal (or the Doppler data) of the blood flowing into the heart.

The ultrasonic diagnostic apparatus 100 (or the control unit 120) may determine, from the Doppler waveform, an opening time (TV open) of the TV 410 (see FIG. 4) and a closing time (TV close) of the TV 410. The closing time (TV close) of the TV 410 and the opening time (TV open) of the TV 410 may be a time when a phase of the Doppler waveform is reversed.

Also, the ultrasonic diagnostic apparatus 100 (or the control unit 120) may define a signal applied at a certain time, before the opening time (TV open) of the TV 410, having a phase same as that after the opening time (TV open) of the TV 410, as a synchronization signal SS. In other words, blood may not flow from the right atrium 45 (see FIG. 4) to the right ventricle 41 until the opening time (TV open) of the TV 410 occurs after the synchronization signal SS, after the closing time (TV close) of the TV 410.

The ultrasonic diagnostic apparatus 100 (or the control unit 120) may determine the Doppler waveform having the "M" pattern and including the closing time (TV close) of the TV 410 and the opening time (TV open) of the TV 410, to be the inflow Doppler signal (or the first Doppler signal or first Doppler data).

Thus, the ultrasonic diagnostic apparatus 100 according to an embodiment may analyze the shape of the Doppler waveform and determine the Doppler signal having the "M" pattern as the inflow Doppler signal (or the first Doppler signal).

The Doppler waveform (or the Doppler ultrasonic image) shown in FIG. 6 is an example and the present disclosure is not limited thereto. According to an embodiment, the Doppler signal of blood flowing into the heart may generate the Doppler waveform in various shapes similar to the "M" pattern.

Figure 7:
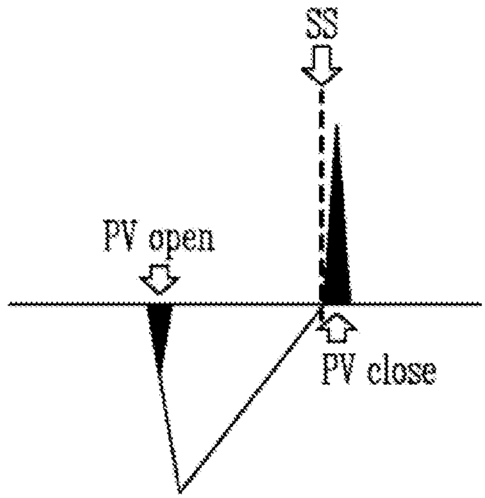
Figure 8:
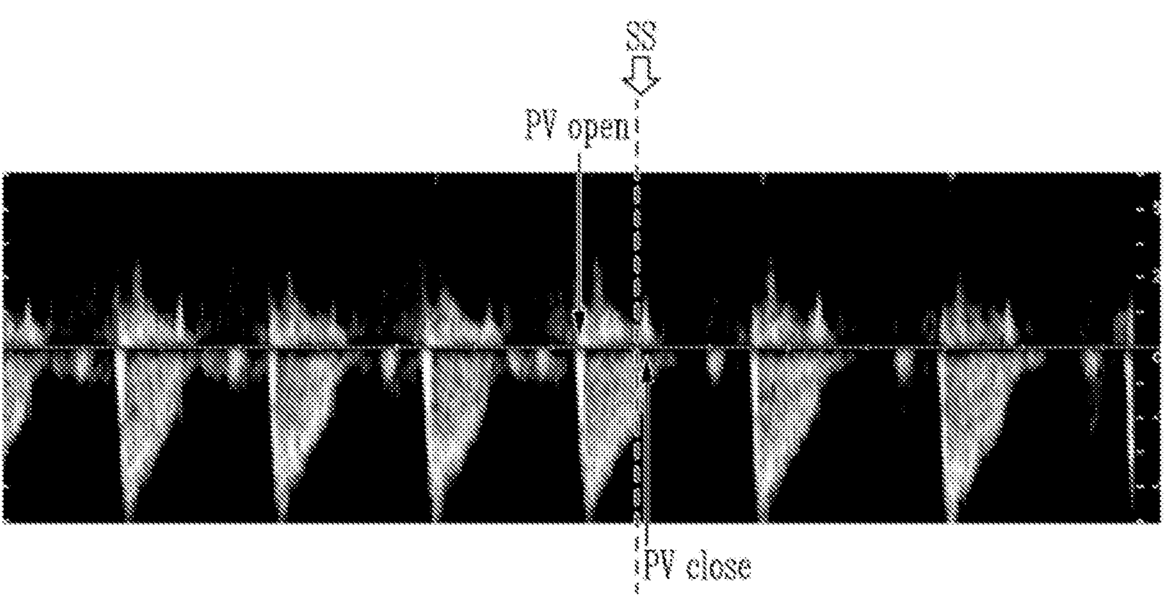

Referring to FIG. 7, a schematic diagram of the Doppler waveform is illustrated, and referring to FIG. 8, the consecutive Doppler ultrasonic images (or Doppler waveforms) are illustrated. The Doppler ultrasonic image may be generated through the control unit 120 and/or the image processing unit 130 as the receiver 115 receives the generated ultrasonic data (or the Doppler signal).

The Doppler waveform shown in FIGS. 7 and 8 may have a "V" pattern. The Doppler waveform having the "V" pattern may be generated based on blood flowing out of the right ventricle 41. In other words, the Doppler waveform having the "V" pattern may be generated based on the Doppler signal (or the Doppler data) of the blood flowing out of the heart.

The ultrasonic diagnostic apparatus 100 (or the control unit 120) may determine, from the Doppler waveform, an opening time (PV open) of the PV 420 (see FIG. 4) and a closing time (PV close) of the PV 420. The opening time (PV open) of the PV 420 and the closing time (PV close) of the PV 420 may be a time when a phase of the Doppler waveform is reversed.

Also, the ultrasonic diagnostic apparatus 100 (or the control unit 120) may define a signal applied at a certain time, before the closing time (PV close) of the PV 420, having a phase same as that after the opening time (PV open) of the PV 420, as the synchronization signal SS. In other words, blood may flow from the right ventricle 41 (see FIG. 4) to the pulmonary artery 44 (see FIG. 4) until the closing time (PV close) of the PV 420 occurring after the synchronization signal SS, after the opening time (PV open) of the PV 420. According to an embodiment, the synchronization signal SS of the Doppler signal of outflow blood may match the closing time (PV close) of the PV 420. However, the present disclosure is not limited thereto.

The ultrasonic diagnostic apparatus 100 (or the control unit 120) may determine the Doppler waveform having the "V" pattern and including the opening time (PV open) of the PV 420 and the closing time (PV close) of the PV 420, to be the outflow Doppler signal (or the second Doppler signal or second Doppler data).

Thus, the ultrasonic diagnostic apparatus 100 according to an embodiment may analyze the shape of the Doppler waveform and determine the Doppler signal having the "V" pattern as the outflow Doppler signal (or the second Doppler signal).

The Doppler waveform (or the Doppler ultrasonic image) shown in FIG. 8 is an example and the present disclosure is not limited thereto. According to an embodiment, the Doppler signal of blood flowing out of the heart may generate the Doppler waveform in various shapes similar to the "V" pattern.

Hereinafter, a method of determining the optimum inflow Doppler signal and the optimum outflow Doppler signal for calculating the measurement area and the measurement index from the inflow Doppler signal and the outflow Doppler signal will be described with reference to FIGS. 9 to 12.

FIGS. 9, 10, 11, and 12 are diagrams for describing a method by which an ultrasonic diagnostic apparatus according to an embodiment determines a Doppler signal suitable for measurement. Hereinafter, an embodiment is described with reference to the components and the reference numerals described with reference to FIGS. 1 to 4.

Figure 9:
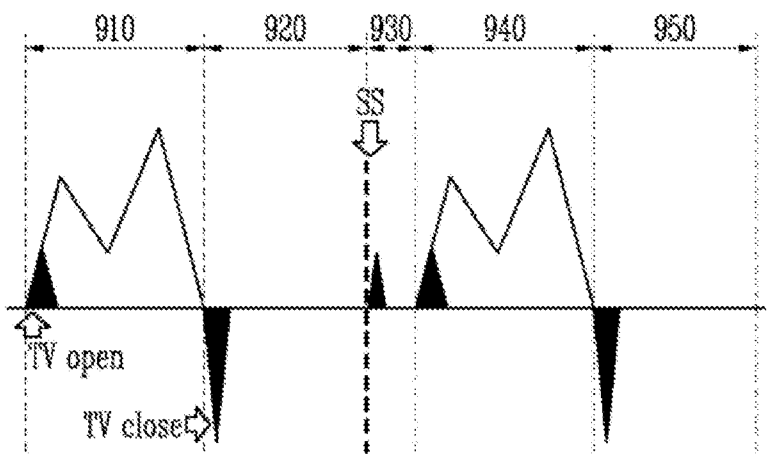
Figure 10:
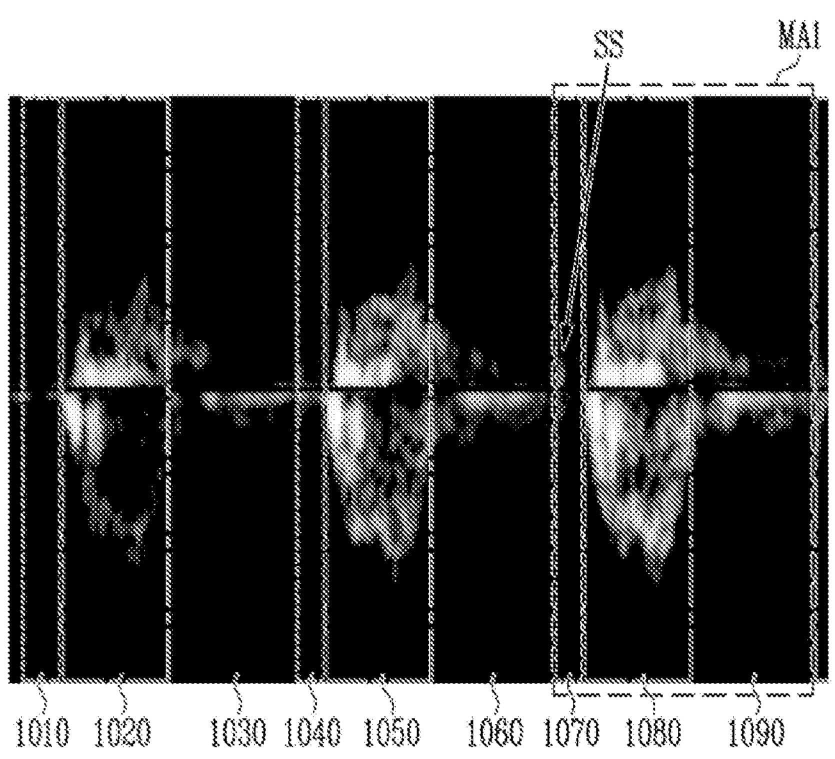

Referring to FIG. 9, a schematic diagram of the inflow Doppler waveform is illustrated, and referring to FIG. 10, the consecutive Doppler ultrasonic images (or Doppler waveforms) are illustrated. The Doppler ultrasonic image shown in FIG. 10 corresponds to the inflow Doppler ultrasonic image determined according to the shape of the Doppler waveform.

According to an embodiment, the Doppler signal suitable for measurement may be extracted based on the cardiac cycle (e.g., from one relaxation of the heart to the next relaxation and from one contraction of the heart to the next contraction), a similarity to a learned Doppler signal, and the strength of the Doppler signal.

The ultrasonic diagnostic apparatus 100 (or the control unit 120) may extract, from the consecutive inflow Doppler signals, the Doppler signal suitable for measurement. The extracting of the Doppler signal suitable for measurement denotes that the Doppler signal suitable for measurement is determined such that the period of the Doppler waveform generated based on the extracted Doppler signal is identical or close to the cardiac cycle, the extracted Doppler signal is similar to the learned Doppler signal, and the strength of the extracted Doppler signal is equal to or greater than certain strength.

The ultrasonic diagnostic apparatus 100 (or the display unit 140) may display the at least one area from the inflow Doppler ultrasonic image such that the consecutive Doppler waveforms (or Doppler signals) are divided into certain areas. Here, the at least one area may be an area located between two straight lines. Each area may be divided according to the shape of the Doppler waveform. Also, each area may be divided according to the Doppler signal information, the cardiac cycle, or the like.

The Doppler waveform shown in FIG. 9 may be positioned at a first reference area 910, a second reference area 920, a third reference area 930, a fourth reference area 940, and a fifth reference area 950.

The first reference area 910 and the fourth reference area 940 may be areas including the opening time (TV open) of the TV 410 (see FIG. 4) and including the Doppler waveform of "M" shape having two peak points.

The second reference area 920 and the fifth reference area 950 may be an area including the closing time (TV close) of the TV 410 and including a shape having one peak point extending from the "M" shape.

The third reference area 930 may be an area including a time when the synchronization signal SS is applied.

The ultrasonic diagnostic apparatus 100 (or the control unit 120) may define one cardiac cycle to be from the synchronization signal SS to immediately before the next opening time (TV open) of the TV 410, and thus, a period including the third reference area 930, the fourth reference area 940, and the fifth reference area 950 may correspond to one cardiac cycle.

The inflow Doppler waveform shown in FIG. 10 may be displayed in a first comparative area 1010, a second comparative area 1020, a third comparative area 1030, a fourth comparative area 1040, a fifth comparative area 1050, a sixth comparative area 1060, a seventh comparative area 1070, an eighth comparative area 1080, and a ninth comparative area 1090.

The first to ninth comparative areas 1010 to 1090 of FIG. 10 may correspond to the first to fifth reference areas 910 to 950 of FIG. 9. In detail, the third reference area 930 of FIG. 9 may correspond to the first comparative area 1010, the fourth comparative area 1040, and the seventh comparative area 1070 of FIG. 10, the first reference area 910 and the fourth reference area 940 of FIG. 9 may correspond to the second comparative area 1020, the fifth comparative area 1050, and the eighth comparative area 1080 of FIG. 10, and the second reference area 920 and the fifth reference area 950 of FIG. 9 may correspond to the third comparative area 1030, the sixth comparative area 1060, and the ninth comparative area 1090 of FIG. 10. Similar shapes of Doppler waveforms may be displayed in the above-described corresponding areas.

Also, the first to third comparative areas 1010 to 1030 of FIG. 10 may correspond to one cardiac cycle, the fourth to sixth comparative areas 1040 to 1060 may correspond to one cardiac cycle, and the seventh to ninth comparative areas 1070 to 1090 may correspond to one cardiac cycle.

The first comparative area 1010, the fourth comparative area 1040, and the seventh comparative area 1070 may be areas including times when the synchronization signal SS is applied. Among the first comparative area 1010, the fourth comparative area 1040, and the seventh comparative area 1070, an area where the synchronization signal SS is displayed dark and bright may correspond to a partial area of a first measurement area MA1. For example, the seventh comparative area 1070 is applied with the synchronization signal SS that is brighter and darker than in the first comparative area 1010 and the fourth comparative area 1040, and thus, the seventh comparative area 1070 may correspond to the partial area of the first measurement area MA1.

The second comparative area 1020, the fifth comparative area 1050, and the eighth comparative area 1080 may be areas including the opening time (TV open) of the TV 410 (see FIG. 4) and including the Doppler waveform of "M" shape having two peak points. Among the second comparative area 1020, the fifth comparative area 1050, and the eighth comparative area 1080, an area where the Doppler waveform of "M" shape having the two peak points is displayed bright and dark may correspond to the partial area of the first measurement area MA1. For example, the eighth comparative area 1080 displays the "M" shape that is brighter and darker than in the second comparative area 1020 and the fifth comparative area 1050, and thus the eighth comparative area 1080 may correspond to the partial area of the first measurement area MA1.

The third comparative area 1030, the sixth comparative area 1060, and the ninth comparative area 1090 may be areas including the closing time (TV close) of the TV 410 and including a shape having one peak point extending from the "M" shape. Among the third comparative area 1030, the sixth comparative area 1060, and the ninth comparative area 1090, an area where the shape having one peak point is displayed bright and dark may correspond to the partial area of the first measurement area MA1. For example, as the sixth comparative area 1060 displays one peak point that is brighter and darker than in the third comparative area 1030 and the ninth comparative area 1090, the sixth comparative area 1060 may correspond to the partial area of the first measurement area MA1.

The ultrasonic diagnostic apparatus 100 (or the control unit 120) may calculate the similarity by comparing the inflow Doppler signal with a pre-learned inflow Doppler signal. The similarity may be calculated for each comparative area of the Doppler ultrasonic image. Here, the similarity denotes a probability of similarity between the inflow Doppler signal and the pre-learned inflow Doppler signal.

Also, the ultrasonic diagnostic apparatus 100 (or the control unit 120) may calculate the similarity for each comparative area, based on the period of the Doppler waveform generated based on the inflow Doppler signal, the cardiac cycle, and the strength of the inflow Doppler signal.

The ultrasonic diagnostic apparatus 100 (or the control unit 120) may determine that the Doppler signal of the comparative area corresponds to the Doppler signal suitable for measurement when the calculated similarity is high. In detail, it may be determined that a Doppler signal in an area, in which an average of the similarity is high, corresponds to the Doppler signal suitable for measurement, in at least one comparative area corresponding to one cardiac cycle.

For example, results of the ultrasonic diagnostic apparatus 100 detecting the similarity for each comparative area shown in FIG. 10 may be indicated as the table below.

TABLE 1

| One Cycle | Similarity |
|---|---|
| First Comparative Area 1010 | 5.51 |
| Second Comparative Area 1020 | 5.86 |
| Third Comparative Area 1030 | 7.21 |
| Fourth Comparative Area 1040 | 7.36 |
| Fifth Comparative Area 1050 | 8.78 |
| Sixth Comparative Area 1060 | 7.89 |
| Seventh Comparative Area 1070 | 8.01 |
| Eighth Comparative Area 1080 | 8.82 |
| Ninth Comparative Area 1090 | 7.46 |

The ultrasonic diagnostic apparatus 100 (or the control unit 120) may determine the first measurement area MA1 from the Doppler ultrasonic image by using the similarity. For example, the ultrasonic diagnostic apparatus 100 (or the control unit 120) may determine, among the first comparative area 1010, the fourth comparative area 1040, and the seventh comparative area 1070, the seventh comparative area 1070 having the highest similarity as the partial area of the first measurement area MA1, and determine, among the second comparative area 1020, the fifth comparative area 1050, and the eighth comparative area 1080, the eighth comparative area 1080 having the highest similarity as the partial area of the first measurement area MA1. However, even when the similarity of the sixth comparative area 1060 is the highest among the third comparative area 1030, the sixth comparative area 1060, and the ninth comparative area 1090, an average value of the similarity of the seventh comparative area 1070 and the eighth comparative area 1080, which constitute one cycle of the first measurement area MA1, is great, and thus, the ninth comparative area 1090 may be determined as the partial area of the first measurement area MA1. Accordingly, the first measurement area MA1 may include the seventh comparative area 1070, the eighth comparative area 1080, and the ninth comparative area 1090.

Figure 11:
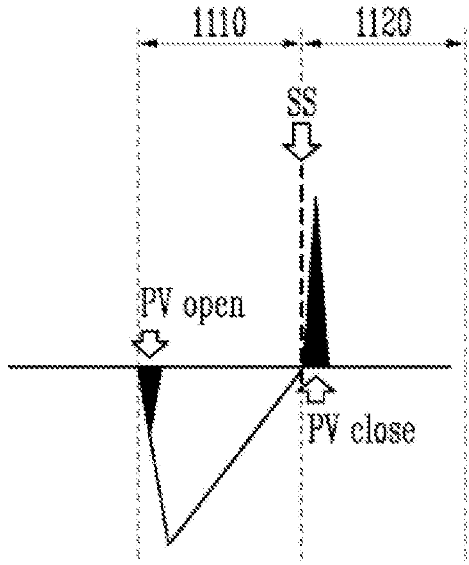
Figure 12:
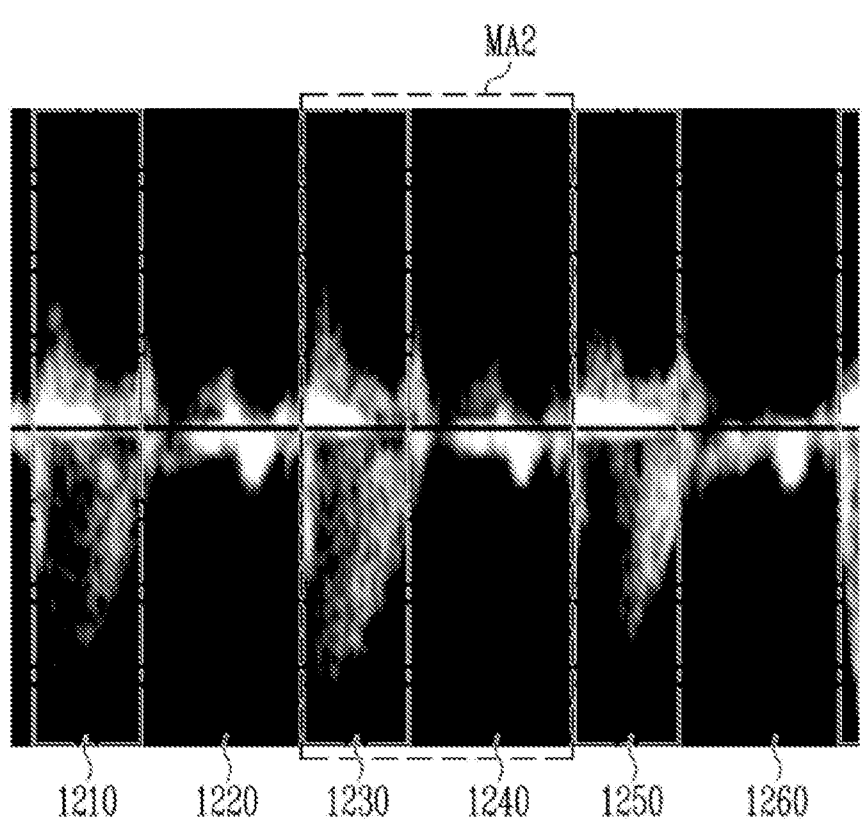

Referring to FIG. 11, a schematic diagram of the outflow Doppler waveform is illustrated, and referring to FIG. 12, the consecutive Doppler ultrasonic images (or Doppler waveforms) are illustrated. The Doppler ultrasonic image shown in FIG. 12 corresponds to the outflow Doppler ultrasonic image determined according to the shape of the Doppler waveform.

The Doppler waveform shown in FIG. 11 may be positioned in a first reference area 1110 and a second reference area 1120.

The first reference area 1110 may be an area including the opening time (PV open) of the PV 420 (see FIG. 4) and including a Doppler waveform of "V" shape having one peak point.

The second reference area 1120 may be an area including the closing time (PV close) of the PV 420 and including a shape having one peak point extending from the "V" shape. The second reference area 1120 may be an area including a time when the synchronization signal SS is applied.

The ultrasonic diagnostic apparatus 100 (or the control unit 120) may define one cardiac cycle to be before the opening time (PV open) of the PV 420 to immediately before the next opening time (PV open) of the PV 420, and thus, a period including the first reference area 1110 and the second reference area 1120 may correspond to one cardiac cycle.

The outflow Doppler waveform shown in FIG. 12 may be displayed in a first comparative area 1210, a second comparative area 1220, a third comparative area 1230, a fourth comparative area 1240, a fifth comparative area 1250, and a sixth comparative area 1260.

The first to sixth comparative areas 1210 to 1260 of FIG. 12 may correspond to the first and second reference areas 1110 and 1120 of FIG. 11. In detail, the first reference area 1110 of FIG. 11 may correspond to the first comparative area 1210, the third comparative area 1230, and the fifth comparative area 1250 of FIG. 12, and the second reference area 1120 may correspond to the second comparative area 1220, the fourth comparative area 1240, and the sixth comparative area 1260. Similar shapes of Doppler waveforms may be displayed in the above-described corresponding areas.

Also, the first comparative area 1210 and the second comparative area 1220 of FIG. 12 may correspond to one cardiac cycle, the third comparative area 1230 and the fourth comparative area 1240 may correspond to one cardiac cycle, and the fifth comparative area 1250 and the sixth comparative area 1260 may correspond to one cardiac cycle.

The first comparative area 1210, the third comparative area 1230, and the fifth comparative area 1250 may be areas including the opening time (PV open) of the PV 420 and including the Doppler waveform of "V" shape having one peak point. Among the first comparative area 1210, the third comparative area 1230, and the fifth comparative area 1250, an area where the Doppler waveform of "V" shape having the one peak point is displayed bright and dark may correspond to a partial area of a second measurement area MA2. For example, the third comparative area 1230 displays the "V" shape that is brighter and darker than in the first comparative area 1210 and the fifth comparative area 1250, and thus, the third comparative area 1230 may correspond to the partial area of the second measurement area MA2.

The second comparative area 1220, the fourth comparative area 1240, and the sixth comparative area 1260 may be areas including the closing time (PV close) of the PV 420 and including a time when the synchronization signal SS is applied. Among the second comparative area 1220, the fourth comparative area 1240, and the sixth comparative area 1260, an area where the synchronization signal SS is displayed dark and bright may correspond to the partial area of the second measurement area MA2. For example, the fourth comparative area 1240 is applied with the synchronization signal SS that is brighter and darker than in the second comparative area 1220 and the sixth comparative area 1260, and thus, the fourth comparative area 1240 may correspond to the partial area of the second measurement area MA2.

The ultrasonic diagnostic apparatus 100 (or the control unit 120) may calculate the similarity by comparing the outflow Doppler signal with the pre-learned outflow Doppler signal. The similarity may be calculated for each comparative area of the Doppler ultrasonic image.

Also, the ultrasonic diagnostic apparatus 100 (or the control unit 120) may calculate the similarity for each comparative area, based on the period of the Doppler waveform generated based on the outflow Doppler signal, the cardiac cycle, and the strength of the outflow Doppler signal.

The ultrasonic diagnostic apparatus 100 (or the control unit 120) may determine that the Doppler signal of the comparative area corresponds to the Doppler signal suitable for measurement when the calculated similarity is high. In detail, it may be determined that a Doppler signal in an area, in which an average of the similarity is high, corresponds to the Doppler signal suitable for measurement, in at least one comparative area corresponding to one cardiac cycle.

For example, results of the ultrasonic diagnostic apparatus 100 detecting the similarity for each comparative area shown in FIG. 12 may be indicated as the table below.

TABLE 2

| One Cycle | Similarity |
|---|---|
| First Comparative Area 1210 | 9.59 |
| Second Comparative Area 1220 | 8.13 |
| Third Comparative Area 1230 | 11.25 |
| Fourth Comparative Area 1240 | 8.39 |
| Fifth Comparative Area 1250 | 7.01 |
| Sixth Comparative Area 1260 | 8.28 |

The ultrasonic diagnostic apparatus 100 (or the control unit 120) may determine the second measurement area MA2 from the Doppler ultrasonic image by using the similarity. For example, the ultrasonic diagnostic apparatus 100 (or the control unit 120) may determine, among the first comparative area 1210, the third comparative area 1230, and the fifth comparative area 1250, the third comparative area 1230 having the highest similarity as the partial area of the second measurement area MA2, and determine, among the second comparative area 1220, the fourth comparative area 1240, and the sixth comparative area 1260, the fourth comparative area 1240 having the highest similarity as the partial area of the second measurement area MA2. Accordingly, the second measurement area MA2 may include the third comparative area 1230 and the fourth comparative area 1240. The second measurement area MA2 may configure the measurement area together with the first measurement area MA1 described above.

The ultrasonic diagnostic apparatus 100 (or the control unit 120) may match the synchronization signal SS of the second measurement area MA2 to the synchronization signal SS of the first measurement area MA1 to determine one measurement area, and calculate the measurement index based on the measurement area. Here, the synchronization signals SS being matched indicates that the synchronization signal SS of the second measurement area MA2 and the synchronization signal SS of the first measurement area MA1 are on the same straight line.

Hereinafter, a method by which the ultrasonic diagnostic apparatus calculates the measurement index, based on the measurement area, will be described with reference to FIGS. 13 and 14.

FIG. 13 is a diagram illustrating a first measurement area and a second measurement area being determined by an ultrasonic diagnostic apparatus according to an embodiment, and FIG. 14 is a diagram for describing a method by which an ultrasonic diagnostic apparatus according to an embodiment calculates a measurement index. Hereinafter, an embodiment is described with reference to the components and the reference numerals described with reference to FIGS. 1 to 4.

Referring to (a) of FIG. 13, the ultrasonic diagnostic apparatus 100 (or the control unit 120) may determine a plurality of areas 1310 and 1320 for the Doppler waveform, based on the inflow Doppler signal information. The plurality of areas 1310 and 1320 may be determined by the method of setting a measurement area, described with reference to FIGS. 9 to 12. Here, the plurality of areas 1310 and 1320 may include a first area 1310 and a second area 1320.

The ultrasonic diagnostic apparatus 100 (or the control unit 120) may calculate the similarity by comparing the inflow Doppler signal with the pre-learned inflow Doppler signal for the plurality of areas 1310 and 1320.

The ultrasonic diagnostic apparatus 100 (or the control unit 120) may determine that the Doppler signal of the corresponding area corresponds to the Doppler signal suitable for measurement when the calculated similarity is high, and determine the measurement area in the Doppler ultrasonic image. For example, among the plurality of areas 1310 and 1320, when the similarity of the second area 1320 is greater than the similarity of the first area 1310, the second area 1320 may be determined as the first measurement area MA1.

Referring to (b) of FIG. 13, the ultrasonic diagnostic apparatus 100 (or the control unit 120) may determine a plurality of areas 1330 and 1340 for the Doppler waveform, based on the outflow Doppler signal information. The plurality of areas 1330 and 1340 may be determined by the method of setting a measurement area, described with reference to FIGS. 9 to 12. Here, the plurality of areas 1330 and 1340 may include a third area 1330 and a fourth area 1340. For example, among the plurality of areas 1330 and 1340, when similarity of the third area 1330 is greater than similarity of the fourth area 1340, the third area 1330 may be determined as the second measurement area MA2.

The ultrasonic diagnostic apparatus 100 (or the control unit 120) may place the synchronization signal SS of the first measurement area MA1 and the synchronization signal SS of the second measurement area MA2 on a same straight line to determine one measurement area, and calculate the measurement index based on the measurement area.

According to an embodiment, the measurement index indicates at least one parameter related to a function of the heart. For example, the at least one parameter may include a tricuspid valve closing time TST, a pulmonary valve opening time ET, a cardiac systolic time ICT, a cardiac diastolic time IRT, and a myocardial performance index MPI.

Referring to FIG. 14, the tricuspid valve closing time TST is a time from immediately before the closing time (TV close) of the TV 410 (see FIG. 4) to immediately before the opening time (TV open) of the TV 410.

The pulmonary valve opening time ET is a time from immediately before the opening time (PV open) of the PV 420 (see FIG. 4) to immediately before the closing time (PV close) of the PV 420.

The cardiac systolic time ICT is a time from immediately before the closing time (TV close) of the TV 410 to immediately before the opening time (PV open) of the PV 420.

The cardiac diastolic time IRT is a time from immediately before the closing time (PV close) of the PV 420 to immediately before the opening time (TV open) of the TV 410.

The myocardial performance index MPI may be calculated by dividing a difference value between the tricuspid valve closing time TST and the pulmonary valve opening time ET by the pulmonary valve opening time ET. Thus, according to an embodiment, the ultrasonic diagnostic apparatus 100 (or the control unit 120) may calculate the myocardial performance index MPI based on a measurement area MA.

In other words, according to an embodiment, the ultrasonic diagnostic apparatus 100 may automatically determine the inflow Doppler signal and the outflow Doppler signal, and automatically calculate the measurement area and the measurement index, based on the optimum inflow Doppler signal and the optimum outflow Doppler signal. Accordingly, the accuracy of the measurement index calculated from the Doppler ultrasonic image may be improved and user convenience may be increased.

Hereinafter, a method by which an ultrasonic diagnostic apparatus analyzes a shape of a Doppler waveform and a method by which an ultrasonic diagnostic apparatus determines a Doppler signal suitable for measurement will be described with reference to FIGS. 15 and 16.

FIG. 15 is a diagram for describing a method by which an ultrasonic diagnostic apparatus according to an embodiment analyzes a shape of a Doppler waveform, and FIG. 16 is a diagram for describing a method by which an ultrasonic diagnostic apparatus according to an embodiment determines a Doppler signal suitable for measurement. Hereinafter, an embodiment is described with reference to the components and the reference numerals described with reference to FIGS. 1 to 4.

Referring to FIG. 15, a schematic diagram of the Doppler waveform is illustrated. The Doppler waveform shown in FIG. 15 may have a pattern in which a phase of an "M" pattern is reversed. In other words, the Doppler waveform shown in FIG. 15 may be a waveform that is the same as that obtained by reversing a phase of the Doppler waveform of FIG. 5 by 180°.

The ultrasonic diagnostic apparatus 100 (or the control unit 120) may determine the Doppler waveform having a "reversed M" pattern as the inflow Doppler signal (or the first Doppler signal or first Doppler data). In other words, the Doppler waveform having the "reversed M" pattern may be generated based on the Doppler signal (or the Doppler data) of the blood flowing into the heart.

Details about the opening time (TV open) of the TV 410 (see FIG. 4), the closing time (TV close) of the TV 410, and the synchronization signal SS are the same as those described with reference to FIG. 5, and thus, repeated descriptions thereof are omitted.

Referring to FIG. 16, the consecutive Doppler ultrasonic images (or Doppler waveforms) and a plurality of areas are illustrated.

The consecutive Doppler ultrasonic images shown in (a) of FIG. 16 may be an inflow Doppler ultrasonic image generated based on the inflow Doppler signal having the "reversed M" pattern.

The plurality of areas (areas between straight lines shown in broken lines) shown in (b) of FIG. 16 are displayed to calculate the measurement area and the measurement index.

The ultrasonic diagnostic apparatus 100 (or the display unit 140) may display at least one area such that the consecutive Doppler waveforms are divided into certain areas.

The ultrasonic diagnostic apparatus 100 (or the control unit 120) may determine the Doppler signal information based on the inflow Doppler signal. Here, the Doppler signal information includes the opening time (TV open) of the TV 410 (see FIG. 4), the closing time (TV close) of the TV 410, and the location of the synchronization signal SS.

Also, the ultrasonic diagnostic apparatus 100 (or the control unit 120) may determine the plurality of areas for the Doppler waveform, based on the determined inflow Doppler signal information. In other words, the plurality of areas may be determined according to the opening time (TV open) of the TV 410, the closing time (TV close) of the TV 410, and the location of the synchronization signal SS.

The ultrasonic diagnostic apparatus 100 (or the control unit 120) may calculate the similarity by comparing the inflow Doppler signal with the pre-learned inflow Doppler signal for each area. The ultrasonic diagnostic apparatus 100 (or the control unit 120) may determine that the Doppler signal of the corresponding area corresponds to the Doppler signal suitable for measurement when the calculated similarity is high.

Also, the ultrasonic diagnostic apparatus 100 (or the control unit 120) may determine the measurement area from the Doppler ultrasonic image by using the similarity. Also, the ultrasonic diagnostic apparatus 100 (or the control unit 120) may calculate the measurement index based on the measurement area. Here, the measurement index is the same as the measurement index described above with reference to FIGS. 13 and 14, and thus, repeated descriptions thereof are omitted.

Hereinafter, a method by which an ultrasonic diagnostic apparatus analyzes a shape of a Doppler waveform and a method by which an ultrasonic diagnostic apparatus determines a Doppler signal suitable for measurement will be described with reference to FIGS. 17 and 18.

FIG. 17 is a diagram for describing a method by which an ultrasonic diagnostic apparatus according to an embodiment analyzes a shape of a Doppler waveform, and FIG. 18 is a diagram for describing a method by which an ultrasonic diagnostic apparatus according to an embodiment determines a Doppler signal suitable for measurement. Hereinafter, an embodiment is described with reference to the components and the reference numerals described with reference to FIGS. 1 to 4.

Referring to FIG. 17, a schematic diagram of the Doppler waveform is illustrated. The Doppler waveform shown in FIG. 17 may have a pattern in which a phase of a "V" pattern is reversed. In other words, the Doppler waveform shown in FIG. 17 may be a waveform that is the same as that obtained by reversing a phase of the Doppler waveform of FIG. 7 by 180°.

The ultrasonic diagnostic apparatus 100 (or the control unit 120) may determine the Doppler waveform having a "reversed V" pattern as the outflow Doppler signal (or the second Doppler signal or second Doppler data). In other words, the Doppler waveform having the "reversed V" pattern may be generated based on the Doppler signal (or the Doppler data) of the blood flowing out from the heart.

Details about the opening time (PV open) of the PV 420 (see FIG. 4), the closing time (PV close) of the PV 420, and the synchronization signal SS are the same as those described with reference to FIG. 7, and thus, repeated descriptions thereof are omitted.

Referring to FIG. 18, the consecutive Doppler ultrasonic images (or Doppler waveforms) and a plurality of areas are illustrated.

The consecutive Doppler ultrasonic images shown in (a) of FIG. 18 may be an outflow Doppler ultrasonic image generated based on the outflow Doppler signal having the "reversed V" pattern.

The plurality of areas (areas between straight lines shown in broken lines) shown in (b) of FIG. 18 are displayed to calculate the measurement area and the measurement index.

The ultrasonic diagnostic apparatus 100 (or the display unit 140) may display the plurality of areas such that the consecutive Doppler waveforms are divided into certain areas. Methods of determining the plurality of areas and the measurement area and calculating the measurement index are the same as those described above with reference to FIGS. 13 and 14, and thus, repeated descriptions thereof are omitted.

Hereinafter, a Doppler ultrasonic image displayed on an ultrasonic diagnostic apparatus will be described with reference to FIGS. 19 to 22.

FIG. 19 is a diagram showing a Doppler ultrasonic image displayed on an ultrasonic diagnostic apparatus according to an embodiment, FIG. 20 is a diagram showing a Doppler ultrasonic image, a measurement area, and a measurement index displayed on an ultrasonic diagnostic apparatus according to an embodiment, FIG. 21 is a diagram showing a Doppler ultrasonic image displayed on an ultrasonic diagnostic apparatus according to an embodiment, and FIG. 22 is a diagram for describing a Doppler ultrasonic image displayed on an ultrasonic diagnostic apparatus according to an embodiment.

Referring to FIG. 19, the ultrasonic diagnostic apparatus (or the display unit 140) may include a main display area 141 and a sub display area 142.

The main display area 141 may be divided into two areas and may include a first main display area 141*a* and a second main display area 141*b*. The first main display area 141*a* may be located at the top of the two areas and the second main display area 141*b* may be located at the bottom of the two areas.

The main display area 141 may display the inflow Doppler ultrasonic image (or the first Doppler ultrasonic image) and/or the outflow Doppler ultrasonic image (or the second Doppler ultrasonic image).

According to an embodiment, when the type of the Doppler signal is automatically determined by the control unit 120 (see FIG. 1) according to the shape of the Doppler waveform, the first main display area 141*a* may display the inflow Doppler ultrasonic image and the second main display area 141*b* may display the outflow Doppler ultrasonic image. Accordingly, the user may intuitively determine that an image displayed on the first main display area 141*a* is the inflow Doppler ultrasonic image and an image displayed on the second main display area 141*b* is the outflow Doppler ultrasonic image only by locations of areas of the main display area 141. Accordingly, the ultrasonic diagnostic apparatus according to an embodiment may enhance user convenience.

The present disclosure is not limited thereto, and the outflow Doppler ultrasonic image may be displayed on the first main display area 141*a* and the inflow Doppler ultrasonic image may be displayed on the second main display area 141*b*, according to an embodiment.

The sub display area 142 may display a plurality of Doppler ultrasonic images. The plurality of Doppler ultrasonic images may include a plurality of inflow Doppler ultrasonic images and a plurality of outflow Doppler ultrasonic images.

The sub display area 142 may display the Doppler ultrasonic image simultaneously with the main display area 141.

When an image is not displayed on the main display area 141, one of the plurality of Doppler ultrasonic images displayed on the sub display area 142 may be selected by a user input and displayed on the main display area 141. Also, one of the plurality of Doppler ultrasonic images of the sub display area 142 may replace an image of the main display area 141, by a user input. Here, the inflow Doppler ultrasonic image may be displayed on the first main display area 141*a* and the outflow Doppler ultrasonic image may be displayed on the second main display area 141*b*. In other words, the user may identify the Doppler ultrasonic image automatically displayed on the main display area 141 and replace the Doppler ultrasonic image displayed on the main display area 141 when it is determined that the Doppler ultrasonic image is not suitable.

The Doppler ultrasonic image determined by the user and/or the control unit 120 may be displayed on the main display area 141 and may be a base image for calculating the measurement area and the measurement index.

Also, the sub display area 142 may solely display the Doppler ultrasonic image even when the main display area 141 does not display any image.

Referring to FIG. 20, the ultrasonic diagnostic apparatus (or the display unit 140) may display the doppler ultrasonic image. The display unit 140 may include the first main display area 141*a*, the second main display area 141*b*, and an auxiliary display area 143.

The first main display area 141*a* may display the inflow Doppler ultrasonic image (or the inflow Doppler waveform). The inflow Doppler ultrasonic image displayed on the first main display area 141*a* may correspond to the inflow Doppler waveform having the "reversed M" pattern described above with reference to FIGS. 15 and 16.

The second main display area 141*b* may display the outflow Doppler ultrasonic image. The outflow Doppler ultrasonic image displayed on the second main display area 141*b* may correspond to the outflow Doppler waveform having the "reversed V" pattern described above with reference to FIGS. 17 and 18.

The ultrasonic diagnostic apparatus 100 (or the control unit 120) may determine at least one area of the Doppler waveform, based on the Doppler signal information, and determine the measurement area by comparing the Doppler signal with the pre-learned Doppler signal for each area.

An area between two straight lines displayed on the first main display area 141*a* may indicate the first measurement area MA1 and an area between two straight lines displayed on the second main display area 141*b* may indicate the second measurement area MA2.

The ultrasonic diagnostic apparatus 100 (or the control unit 120) may calculate the measurement index based on the first measurement area MA1 and the second measurement area MA2. Here, details about a method of calculating the measurement index and the calculated measurement index are the same as those described above with reference to FIGS. 13 and 14, and thus, repeated descriptions thereof are omitted.

The auxiliary display area 143 may display the measurement index. Accordingly, the user may determine the tricuspid valve closing time TST, the pulmonary valve opening time ET, the cardiac systolic time ICT, the cardiac diastolic time IRT, and the myocardial performance index MPI through the auxiliary display area 143.

In other words, according to an embodiment, the ultrasonic diagnostic apparatus 100 may automatically determine the inflow Doppler signal and the outflow Doppler signal, automatically calculate the measurement area and the measurement index, based on the optimum inflow Doppler signal and the optimum outflow Doppler signal, and display the same. Accordingly, the accuracy of the measurement index calculated from the Doppler ultrasonic image may be improved and user convenience may be increased.

Referring to FIG. 21, the ultrasonic diagnostic apparatus (or the display unit 140) may include the main display area 141 and the sub display area 142.

The main display area 141 may be divided into two areas and may include the first main display area 141*a* and the second main display area 141*b*.

The sub display area 142 may display the plurality of Doppler ultrasonic images. The plurality of Doppler ultrasonic images may include the plurality of inflow Doppler ultrasonic images and the plurality of outflow Doppler ultrasonic images.

The first main display area 141*a* may display the inflow Doppler ultrasonic image (or the first Doppler ultrasonic image) and the second main display area 141*b* may display the outflow Doppler ultrasonic image (or the second Doppler ultrasonic image). The first main display area 141*a* and the second main display area 141*b* may simultaneously display the Doppler ultrasonic image or only one main display area may display the Doppler ultrasonic image.

According to an embodiment, when the type of the Doppler signal is automatically determined by the control unit 120 (see FIG. 1) according to the shape of the Doppler waveform, the main display area 141 may display a different type of Doppler ultrasonic image from the sub display area 142. Here, the Doppler ultrasonic image displayed on the main display area 141 may be a Doppler ultrasonic image based on a Doppler signal transmitted in real time, and the Doppler ultrasonic image displayed on the sub display area 142 may be a Doppler ultrasonic image based on a Doppler signal pre-stored in the control unit 120 (see FIG. 1), the storage unit 150 (see FIG. 1), or the like.

For example, when the first main display area 141*a* displays the inflow Doppler ultrasonic image, the sub display area 142 may display at least one outflow Doppler ultrasonic image. In other words, the first main display area 141*a* of FIG. 21 may display the inflow Doppler ultrasonic image and the sub display area 142 may display the outflow Doppler ultrasonic images.

Also, when the second main display area 141*b* displays the outflow Doppler ultrasonic image, the sub display area 142 may display at least one inflow Doppler ultrasonic image.

Accordingly, the user may intuitively determine that an image displayed on the first main display area 141*a* is the inflow Doppler ultrasonic image and an image displayed on the second main display area 141*b* is the outflow Doppler ultrasonic image only by locations of areas of the main display area 141. Accordingly, the ultrasonic diagnostic apparatus according to an embodiment may enhance user convenience.

(a) of FIG. 22 is a diagram schematically showing a structure of the heart of a person among objects to which the ultrasonic diagnostic apparatus is applied, (b) of FIG. 22 is a diagram showing a sample volume gate for obtaining the Doppler signal from the heart of the person, and (c) of FIG. 22 is a diagram showing the Doppler ultrasonic image based on the obtained Doppler signal.

Referring to (a) of FIG. 22, the TV 410 located between the right atrium and the left atrium, and the PV 420 located between the right ventricle and the pulmonary artery are displayed. According to an embodiment, information about a closing time and an opening time of the TV 410 may be obtained through the inflow Doppler ultrasonic image. Also, information about the closing time and the opening time of the PV 420 may be obtained through the outflow Doppler ultrasonic image.

Referring to (b) of FIG. 22, a first sample volume gate 221 may be located at the TV 410 and a second sample volume gate 222 may be located at the PV 420. The present disclosure is not limited thereto, and the second sample volume gate 222 may be located at the TV 410 and the first sample volume gate 221 may be located at the PV 420.

According to an embodiment, the inflow Doppler signal flowing into the heart may be obtained from the first sample volume gate 221, and the outflow Doppler signal flowing out from the heart may be obtained from the second sample volume gate 222. Also, when the second sample volume gate 222 is located at the TV 410, the inflow Doppler signal may be obtained from the second sample volume gate 222, and when the first sample volume gate 221 is located at the PV 420, the outflow Doppler signal may be obtained from the first sample volume gate 221.

In other words, the control unit 120 (see FIG. 1) may determine the Doppler signal as the inflow Doppler signal or the outflow Doppler signal, according to the shape of the Doppler waveform, regardless of the locations of the first sample volume gate 221 and the second sample volume gate 222.

The display unit 140 may display the inflow Doppler ultrasonic image in the first main display area 141*a* and display the outflow Doppler ultrasonic image in the second main display area 141*b*.

In other words, the display unit 140 may display the Doppler ultrasonic images in the first main display area 141*a* and the second main display area 141*b*, based on the type of the Doppler signal transmitted from the control unit 120, regardless of the locations of the first sample volume gate 221 and the second sample volume gate 222.

Accordingly, the user may determine the tricuspid valve closing time TST from the inflow Doppler ultrasonic image displayed in the first main display area 141*a*, and determine the pulmonary valve opening time ET from the outflow Doppler ultrasonic image displayed in the second main display area 141*b*. The control unit 120 may calculate the myocardial performance index through the tricuspid valve closing time TST, the pulmonary valve opening time ET, and the like.

In other words, according to an embodiment, the ultrasonic diagnostic apparatus 100 may automatically determine the inflow Doppler signal and the outflow Doppler signal, automatically calculate the measurement area and the measurement index, based on the optimum inflow Doppler signal and the optimum outflow Doppler signal, and display the same. Accordingly, the accuracy of the measurement index calculated from the Doppler ultrasonic image may be improved and the user convenience may be increased. Hereinafter, a learning algorithm for describing a pre-trained method will be described with reference to FIG. 23.

FIG. 23 is a diagram for describing a learning algorithm according to an embodiment.

Referring to FIG. 23, an example of the learning algorithm including at least one hidden layer HDL between an input layer INL and an output layer OTL is illustrated.

The learning algorithm may be recorded on a recording medium and executed by the ultrasonic diagnostic apparatus 100. The recording medium may correspond to the storage unit 150 (see FIG. 1) of the ultrasonic diagnostic apparatus 100. The recording medium may be embedded in an external server of the ultrasonic diagnostic apparatus 100 and the ultrasonic diagnostic apparatus 100 may execute the learning algorithm by communicating with the external server through the communication unit 160 (see FIG. 1).

The recording medium includes any type of recording device capable of storing data, an algorithm, or a program readable by a computer system. Examples of a computer-readable recording medium include read-only memory (ROM), random access memory (RAM), compact disk read-only memory (CD-ROM), a magnetic tape, a floppy disk, an optical data storage device, a hard disk, an external hard disk, a solid state drive (SSD), a universal serial bus (USB) storage device, a digital versatile disk (DVD), and Blu-ray. Also, the computer-readable recording medium may be a combination of a plurality of devices and may be distributed in a computer system connected through a network. Such a recording medium may be a non-transitory computer-readable recording medium. The non-transitory computer-readable recording medium denotes a computer-readable medium that semi-permanently stores data or a program, rather than a medium that instantaneously stores data or a program, like a register, a cache, or a memory.

The input layer INL may include first inputs IN11 to IN1*n* and a second input IN2. The hidden layer HDL may include a plurality of nodes ND11 to ND15. The output layer OTL may include first outputs OT11 to OT15. The numbers of inputs, nodes, and outputs may vary according to embodiments. Also, whether layers are fully connected or connected in another manner may be determined according to embodiments. The learning algorithm according to the present embodiment may be referred to as shallow learning or deep learning depending on the number of hidden layers HDL.

The learning algorithm may include receiving the Doppler signal as the first inputs IN11 to IN1*n* of the input layer INL. Also, the learning algorithm may include receiving a user input as the second input IN2 of the input layer INL.

The learning algorithm may include displaying the Doppler ultrasonic image, based on the first inputs IN11 to IN1*n*, and providing the same as the first outputs OT11 to OT15 of the output layer OTL to display the measurement area and the measurement index on the Doppler ultrasonic image.

Relationships between the first inputs IN11 to IN1*n*, the second input IN2, and the first outputs OT11 to OT15 may be determined according to correlations between the layers INL, HDL, and OTL, weights, and biases.

For example, the Doppler ultrasonic image may be determined by analyzing the shape of the Doppler waveform based on the Doppler signal. Also, the measurement area may be determined based on the Doppler signal information, and the optimum measurement area for determining the measurement index may be selected and the measurement index may be calculated based on the selected measurement area.

Also, the Doppler ultrasonic image determined by the second input IN2 may be replaced and the measurement area may be replaced.

According to an embodiment, the ultrasonic diagnostic apparatus 100 may automatically determine the inflow Doppler signal and the outflow Doppler signal, automatically calculate the measurement area and the measurement index, based on the optimum inflow Doppler signal and the optimum outflow Doppler signal, and display the same. Accordingly, the accuracy of the measurement index calculated from the Doppler ultrasonic image may be improved and user convenience may be increased.

Meanwhile, the embodiments may be implemented in the form of a recording medium storing instructions executable by a computer. The instructions may be stored in the form of a program code and may perform operations of the embodiments by generating a program module when executed by a processor. The recording medium may be realized as a computer-readable recording medium.

Examples of the computer-readable recording medium include any type of recording medium storing instructions capable of being interpreted by a computer. For example, there may be read-only memory (ROM), random access memory (RAM), a magnetic tape, a magnetic disk, a flash memory, and an optical data storage device.

The embodiments have been described above with reference to the accompanying drawings. One of ordinary skill in the art would understand that the present disclosure may be executed in the form different from the embodiments without changing the technical ideas or essential features of the present disclosure. The embodiments are only examples and should not be limitedly interpreted.

The invention claimed is:

1. An ultrasonic diagnostic apparatus comprising:

a display unit; and a control unit configured to:

display a user interface for calculating a measurement index related to a cardiac function of an object based on an inflow Doppler waveform corresponding to blood flowing into a heart of the object and an outflow Doppler waveform corresponding to blood flowing out of the heart of the object, the user interface comprises a display region configured to display the inflow Doppler waveform, a display region configured to display the outflow Doppler waveform and a list of a plurality of Doppler waveforms, the plurality of Doppler waveforms include at least one inflow Doppler waveform and at least one outflow Doppler waveform;

receive a user input of selecting a Doppler waveform from among the plurality of Doppler waveforms;

determine whether the selected Doppler waveform corresponds to the inflow Doppler waveform or the outflow Doppler waveform based on a shape of an envelope of the selected Doppler waveform;

based on determining that the selected Doppler waveform corresponds to the inflow Doppler waveform, display, through the display unit, the selected Doppler waveform on the display region configured to display the inflow Doppler waveform, and based on determining that the selected Doppler waveform corresponds to the outflow Doppler waveform, display through the display unit, the selected Doppler waveform on the display region configured to display the outflow Doppler waveform.

2. The ultrasonic diagnostic apparatus of claim 1, wherein the control unit is further configured to determine at least one period of the selected Doppler waveform.

3. The ultrasonic diagnostic apparatus of claim 2, wherein the control unit is further configured to determine the at least one period of the selected Doppler waveform based on a similarity between the selected Doppler waveform and a pre-learned Doppler waveform.

4. The ultrasonic diagnostic apparatus of claim 3, wherein the control unit is further configured to calculate the similarity for the selected Doppler waveform, based on a period of the selected Doppler waveform for a cardiac cycle of the object, and a strength of a Doppler signal of the selected Doppler waveform.

5. The ultrasonic diagnostic apparatus of claim 1, wherein the control unit is further configured to:

determine the selected Doppler signal as a Doppler waveform as the inflow Doppler waveform based on the shape of the envelope of the selected Doppler waveform being "M" or "reversed M"; and determine the selected Doppler waveform as the outflow Doppler waveform based on the shape of the envelope of the selected Doppler waveform being "V" or "reversed V".

6. The ultrasonic diagnostic apparatus of claim 1, wherein the inflow Doppler waveform comprises an opening time of a tricuspid valve, a closing time of the tricuspid valve, and a location of a synchronization signal, and the outflow Doppler waveform comprises an opening time of a pulmonary valve, a closing time of the pulmonary valve, and the location of the synchronization signal.

7. The ultrasonic diagnostic apparatus of claim 1, wherein the measurement index related to the cardiac function of the object comprises at least one of a tricuspid valve closing time (TST), a pulmonary valve opening time (ET), a cardiac systolic time (ICT), a cardiac diastolic time (IRT), and a myocardial performance index (MPI).

8. The ultrasonic diagnostic apparatus of claim 7, wherein the display unit further displays the measurement index.

9. The ultrasonic diagnostic apparatus of claim 1, wherein the list of the plurality of Doppler waveforms includes each of the plurality of Doppler waveforms and an ultrasound image in which a position of a sample volume gate corresponding to each of the Doppler waveform is displayed.

10. The ultrasonic diagnostic apparatus of claim 9, wherein, when a sample volume gate corresponding to the selected Doppler waveform is located in correspondence to a tricuspid valve, the selected Doppler waveform is displayed on the display region configured to display the inflow Doppler waveform, and when the sample volume gate corresponding to the selected Doppler waveform is located in correspondence to a pulmonary valve, the selected Doppler waveform is displayed on the display region configured to display the outflow Doppler waveform.

11. An operating method of an ultrasonic diagnostic apparatus, the operating method comprising:

displaying a user interface for calculating a measurement index related to a cardiac function of an object based on an inflow Doppler waveform corresponding to blood flowing into a heart of the object and an outflow Doppler waveform corresponding to blood flowing out of the heart of the object, the user interface includes a display region configured to display the inflow Doppler waveform, a display region configured to display the outflow Doppler waveform and a list of a plurality of Doppler waveforms, the plurality of Doppler waveforms include at least one inflow Doppler waveform and at least one outflow Doppler waveform;

receiving a user input of selecting a Doppler waveform from among the plurality of Doppler waveforms;

determining whether the selected Doppler waveform corresponds to the inflow Doppler waveform or the outflow Doppler waveform based on a shape of an envelope of the selected Doppler waveform;

based on determining that the selected Doppler waveform corresponds to the inflow Doppler waveform, displaying, through a display unit, the selected Doppler waveform on the display region configured to display the inflow Doppler waveform, and based on determining that the selected Doppler waveform corresponds to the outflow Doppler waveform, displaying, through the display unit, the selected Doppler waveform on the display region configured to display the outflow Doppler waveform.

12. The operating method of claim 11, further comprising:

determining at least one period of the selected Doppler waveform.

13. The operating method of claim 12, wherein further comprising:

determining the at least one period of the selected Doppler waveform based on a similarity between the selected Doppler waveform and a pre-learned Doppler waveform.

14. The operating method of claim 13, wherein the determining the at least one period of the selected Doppler waveform based on the similarity comprises calculating the similarity for the selected Doppler waveform, based on a period of the selected Doppler waveform a cardiac cycle of the object, and a strength of a Doppler signal of the selected Doppler waveform.

15. The operating method of claim 11, wherein the determining whether the selected Doppler waveform corresponds to the inflow Doppler waveform or the outflow Doppler waveform based on the shape of the envelope of the selected Doppler waveform comprises determining the selected Doppler waveform as the inflow Doppler waveform based on the shape of the envelope of the selected Doppler waveform being "M" or "reversed M" and determining the selected Doppler waveform as the outflow Doppler waveform based on the shape of the envelope of the selected Doppler waveform being "V" or "reversed V".

16. The operating method of claim 11, wherein the inflow Doppler waveform comprises an opening time of a tricuspid valve, a closing time of the tricuspid valve, and a location of a synchronization signal, and the outflow Doppler waveform comprises an opening time of a pulmonary valve, a closing time of the pulmonary valve, and the location of the synchronization signal.

17. The operating method of claim 11, wherein the measurement index related to the cardiac function of the object comprises at least one of a tricuspid valve closing time (TST), a pulmonary valve opening time (ET), a cardiac systolic time (ICT), a cardiac diastolic time (IRT), and a myocardial performance index (MPI).

18. The operating method of claim 17, wherein further comprising:

displaying the measurement index.

19. The operating method of claim 11, wherein the list of the plurality of Doppler waveforms includes each of the plurality of Doppler waveforms and an ultrasound image in which a position of a sample volume gate corresponding to each of the Doppler waveform is displayed.

20. The operating method of claim 19, wherein, when a sample volume gate corresponding to the selected Doppler waveform is located in correspondence to a tricuspid valve, the selected Doppler waveform is displayed on the display region configured to display the inflow Doppler waveform, and when the sample volume gate corresponding to the selected Doppler waveform is located in correspondence to a pulmonary valve, the selected Doppler waveform is displayed on the display region configured to display the outflow Doppler waveform.

* * * * *